US008321032B2

(12) United States Patent
Frysz et al.

(10) Patent No.: US 8,321,032 B2
(45) Date of Patent: *Nov. 27, 2012

(54) RFID-ENABLED AIMD PROGRAMMER SYSTEM FOR IDENTIFYING MRI COMPATIBILITY OF IMPLANTED LEADS

(75) Inventors: Christine A. Frysz, Orchard Park, NY (US); Robert A. Stevenson, Canyon Country, CA (US); Warren S. Dabney, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 138 days.

This patent is subject to a terminal disclaimer.

(21) Appl. No.: 12/871,201

(22) Filed: Aug. 30, 2010

(65) Prior Publication Data

US 2011/0029043 A1    Feb. 3, 2011

Related U.S. Application Data

(63) Continuation-in-part of application No. 11/943,470, filed on Nov. 20, 2007, now Pat. No. 7,787,958, and a continuation-in-part of application No. 12/719,630, filed on Mar. 8, 2010, which is a continuation-in-part of application No. 12/407,402, filed on Mar. 19, 2009, now Pat. No. 8,195,295, said application No. 11/943,470 is a continuation-in-part of application No. 11/558,349, filed on Nov. 9, 2006, now Pat. No. 7,945,322.

(60) Provisional application No. 61/240,864, filed on Sep. 9, 2009.

(51) Int. Cl.
*A61N 1/00* (2006.01)

(52) U.S. Cl. ........................................................ 607/115

(58) Field of Classification Search .................. 607/115
See application file for complete search history.

(56) References Cited

U.S. PATENT DOCUMENTS

| | | | |
|---|---|---|---|
| 6,968,235 B2 * | 11/2005 | Belden et al. | 607/60 |
| 7,429,920 B2 * | 9/2008 | Smythe et al. | 340/539.12 |
| 7,751,903 B2 | 7/2010 | Stevenson et al. | |
| 2010/0123547 A1 | 5/2010 | Stevenson et al. | |
| 2010/0174349 A1 | 7/2010 | Stevenson et al. | |

* cited by examiner

*Primary Examiner* — George Manuel
(74) *Attorney, Agent, or Firm* — Michael F. Scalise

(57) ABSTRACT

An RFID tag is associated with an implantable lead, its sensing or therapy delivery electrode, or a patient, for identifying the MRI compatibility of the implantable lead and/or the presence of a bandstop filter and its attendant characteristics. An RFID-enabled AIMD external telemetry programmer transmits an electromagnetic signal to establish a communication link with the RFID tag.

39 Claims, 14 Drawing Sheets

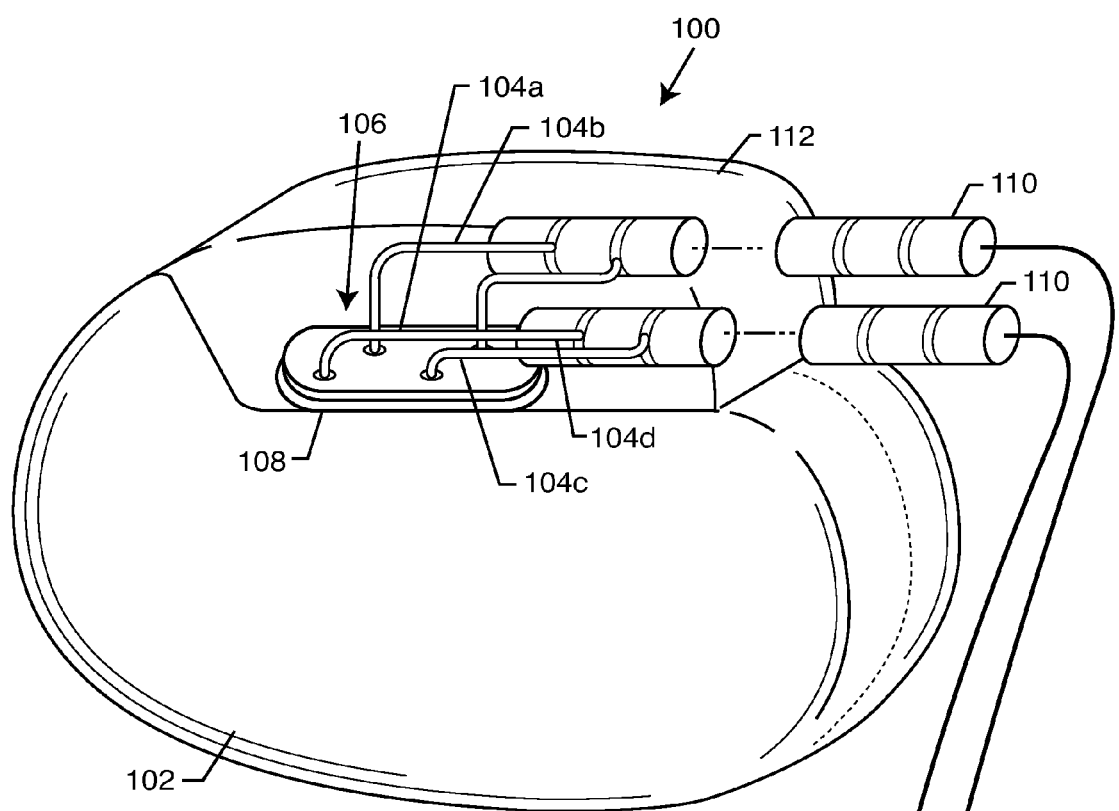
FIG. 2
PRIOR ART
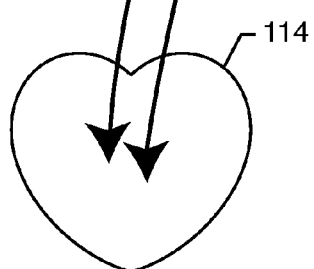

Number of Tanks = $T = T_1 + T_2 + \ldots T_n$

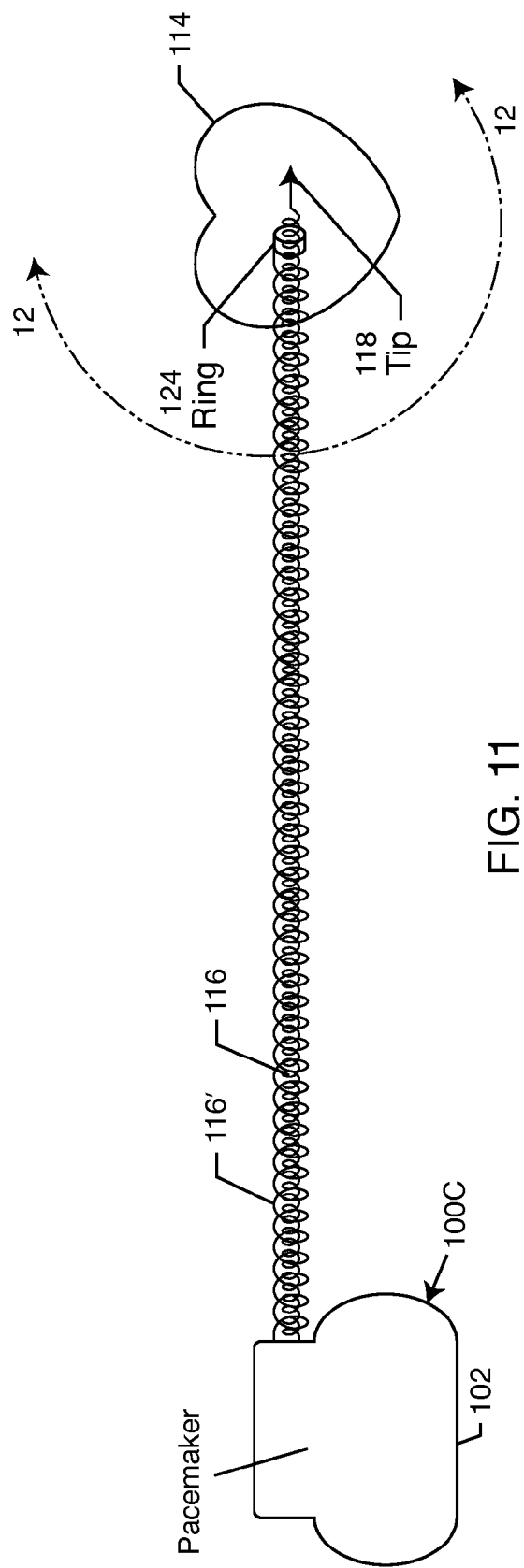
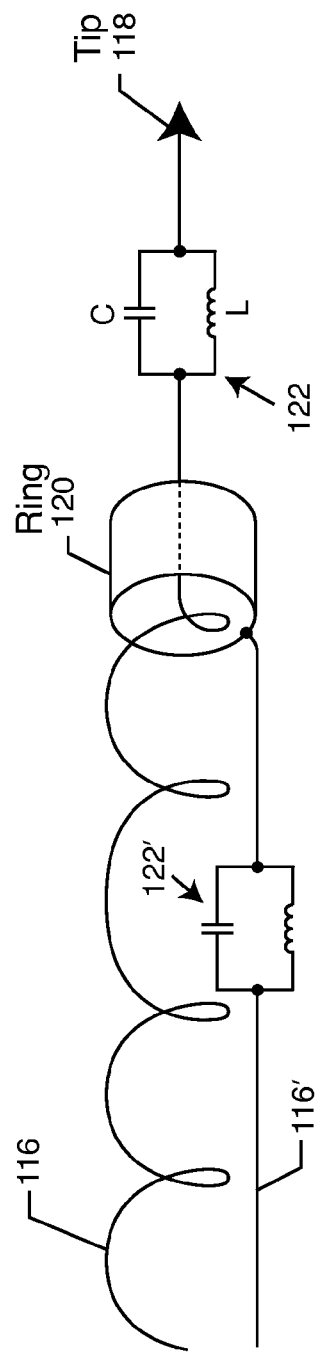
FIG. 11
FIG. 12

RFID-ENABLED AIMD PROGRAMMER SYSTEM FOR IDENTIFYING MRI COMPATIBILITY OF IMPLANTED LEADS

FIELD OF THE INVENTION

This invention relates generally to RFID-enabled active implantable medical device (AIMD) external telemetry programmers. In particular, the AIMD external telemetry programmer includes design modifications for communicating with an implanted RFID tag, wherein the RFID tag contains information about the MRI compatibility of an implanted lead. In this regard, the RFID tag may contain information about an implanted bandstop filter which is located between the distal and proximal end of the implanted AIMD lead.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific CRM (formerly Guidant), one will see that the use of MRI is generally contra-indicated with pacemakers and implantable defibrillators. A similar contra-indication is found in the manuals of MRI equipment manufacturers such as Siemens, GE, and Phillips. See also "Safety Aspects of Cardiac Pacemakers in Magnetic Resonance Imaging", a dissertation submitted to the Swiss Federal Institute of Technology Zurich presented by Roger Christoph Lüchinger. "Dielectric Properties of Biological Tissues: I. Literature Survey", by C. Gabriel, S. Gabriel and E. Cortout; "Dielectric Properties of Biological Tissues: II. Measurements and the Frequency Range 0 Hz to 20 GHz", by S. Gabriel, R. W. Lau and C. Gabriel; "Dielectric Properties of Biological Tissues: Ill. Parametric Models for the Dielectric Spectrum of Tissues", by S. Gabriel, R. W. Lau and C. Gabriel; and "Advanced Engineering Electromagnetics, C. A. Balanis, Wiley, 1989, all of which are incorporated herein by reference.

However, an extensive review of the literature indicates that MRI is indeed often used with pacemaker patients in spite of the contra indications. The safety and feasibility of MRI in patients with cardiac pacemakers is an issue of gaining significance. The effects of MRI on patients' pacemaker systems have only been analyzed retrospectively in some case reports. MRI is one of medicine's most valuable diagnostic tools. MRI is, of course, extensively used for imaging, but is also increasingly used for real-time procedures such as interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. However, because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the applied power of the MRI in terms of the specific absorption rate—SAR programming the pacemaker to fixed or asynchronous pacing mode, having emergency personnel and resuscitation equipment standing by (known as "Level II" protocol), and careful reprogramming and evaluation of the pacemaker and patient after the procedure is complete. There have been reports of latent problems with cardiac pacemakers after an MRI procedure occurring many days later (such as increase in or loss of pacing pulse capture).

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in routine clinical use.

The second type of field produced by magnetic resonance imaging equipment is the pulsed RF field which is generated by the body coil or head coil, also referred to as $B_1$. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. The frequency of the RF pulsed varies with the field strength of the main static field, as expressed in the Lamour Equation: RF PULSED FREQUENCY (in MHz)= (MRI CONSTANT) (STATIC FIELD STRENGTH (T).

The third type of electromagnetic field is the time-varying magnetic gradient field designated $G_{x, y, z}$ which is used for spatial localization. The gradient field changes its strength along different orientations and operating frequencies on the order of 1 to 2.2 kHz.

At the pulsed RF frequencies of interest in MRI, RF energy can be absorbed and converted to heat. The power deposited by RF pulses during MRI is complex and is dependent upon the power, duration and shape of the RF pulse, the relative long term time averages of the pulses, the transmitted frequency, the number of RF pulses applied per unit time, and the type of configuration of the RF transmitter coil used. Specific absorption rate (SAR) is a measure of how much energy is induced into body tissues. The amount of heating also depends upon the volume of the various tissue (i.e. muscle, fat, etc.) imaged, the electrical resistivity of tissue and the configuration of the anatomical region imaged. There are also a number of other variables that depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Location within the MRI bore is also important since the electric fields required to generate the RF increase exponentially as the patient is moved away from MRI bore centerline (ISO center). The cause of heating in an MRI environment is twofold: (a) RF field coupling to the lead can occur which induces significant local heating; and (b) currents induced during the RF transmission can flow into body tissue and cause local Ohm's Law heating next to the distal TIP electrode of the implanted lead. The RF field in an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold, venous ablation, Larynx ablation, myocardial perforation and lead penetration, or even arrhythmias caused by scar tissue. Such long term heating effects of MRI have not been well studied yet.

It has been observed that the RF field may induce undesirable fast cardiac pacing (QRS complex) rates. There are various mechanisms which have been proposed to explain rapid pacing: direct tissue stimulation, interference with pacemaker electronics or pacemaker reprogramming (or reset). In all of these cases, it would be desirable to raise the lead system impedance (to reduce RF current), make the feedthrough capacitor more effective and provide a very high degree of protection to AIMD electronics. This will make alterations in pacemaker pacing rate and/or pacemaker reprogramming much more unlikely.

As one can see, many of the undesirable effects in an implanted lead wire system from MRI and other medical diagnostic procedures are related to undesirable induced currents in the lead wire system. This can lead to overheating either in the lead wire or at the tissue interface at the distal Tip electrode.

Bandstop filters employing a capacitor and an inductor tank circuit can be used to enhance the MRI compatibility of active implantable medical device implanted leads. These are described in U.S. Pat. No. 7,363,090, the contents of which are incorporated herein. The bandstop filters of the '090 patent are designed to be resonant at a selected MRI RF pulse center frequency. The bandstop filters are effective over a range of selected RF pulsed frequencies, which means that they have a broad enough bandwidth to accommodate most manufacturers of 1.5 Tesla rated scanners. The bandstop filters could also be designed for 3 Tesla, 5 Tesla, or other specified scanners. However, it would be exceedingly dangerous to assume that if an implanted lead bandstop filter was rated for 3 Tesla that one could safely perform 1.5 Tesla scans. This is because the RF pulsed frequency between a 3 Tesla and a 1.5 Tesla scanner is very different (approximately 128 MHz for a 3 Tesla and approximately 64 MHz for a 1.5 Tesla). A bandstop filter designed to be resonant for 3 Tesla systems and present a very high impedance, would undesirably present a very low impedance at 1.5 Tesla.

Accordingly, there is a need for a rapid and convenient means of identification of the MRI compatibility of an implanted lead and, in particular, its associated bandstop filter. Moreover, there is a need for a means of rapidly identifying the type of bandstop filter that is associated with an implanted lead and its MRI compatibility. The present invention fulfills these needs and provides other related advantages.

SUMMARY OF THE INVENTION

The present invention is directed to an RFID enabled AIMD programmer system for identifying MRI compatibility of an implantable lead. The system comprises, generally, (1) an implantable lead including an electrode in contact with a patient's body tissue, (2) an RFID tag associated with the implantable lead, the electrode, or the patient, for identifying the MRI compatibility of the implantable lead, (3) an RFID-enabled AIMD external telemetry programmer which transmits an electromagnetic signal to establish a communication link with the RFID tag. The implantable lead may comprise a lead connected to an active implantable medical device (AIMD), an abandoned lead, a lead connected to an abandoned lead cap, or a lead coupled to an active external medical device.

In one preferred embodiment, system comprises, generally, (1) an active implantable medical device (AIMD) including electronic circuitry for therapy delivery or detection of biological signals, an electrode, and an implantable lead for connecting the electrode to the electronic circuitry, (2) a bandstop filter placed in series with the lead and having electrical inductance in parallel with capacitance, whereby the bandstop filter is resonant at a center frequency and attenuates current flow over a range of selected frequencies, (3) an RFID tag associated with the patient, the AIMD, the lead or the electrode, for identifying the presence of the bandstop filter in the AIMD or the lead or the electrode, and (4) an RFID-enabled external AIMD telemetry programmer which transmits an electromagnetic signal to establish a communication link with the AIMD RFID chip.

The electromagnetic signal may comprise an RFID communication signal such as an RFID interrogation signal, an RFID tag search signal, an RFID test signal, an RFID read signal, or an RFID write signal. Preferably, the electromagnetic signal comprises a modulated signal, however, it may be continuous wave.

The AIMD telemetry programmer may comprise a read-only or a reader/writer device, and may be in communication with a computer or a computer network. An electronic database or look-up table enables communication between the AIMD universal programmer and the RFID tag. The electronic database or look-up table may reside in the computer or the computer network, or alternatively, in the RFID-enabled AIMD external telemetry programmer.

The RFID tag may be incorporated with the active implantable medical device, on or in the lead, or it may be implanted into a patient's tissues, or it may be contained on the patient. The RFID tag identifies the MRI compatibility such as 1.5 Tesla and/or bandstop filter center frequency or a selected range of frequencies.

The RFID-enabled AIMD external telemetry programmer may be configured to actively search for or communicate with the RFID tag. The RFID tag may comprise an antenna and an electronic micro-chip electrically connected to the antenna. The RFID tag may be associated with an object in close proximity to a patient having an active implantable medical device. The RFID tag is associated with the active implantable medical device lead(s) and may include retrievable information relating to the AIMD and/or the patient and/or the physician. The retrievable information includes information pertaining to magnetic resonance imaging (MRI) compatibility of the AIMD and/or its associated lead system. Means may also be provided for changing information stored in the RFID tag to correspond to changes in characteristics of the AIMD, and associated lead system or the patient.

The AIMD may comprise a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, an endovascular catheter, a bion or a prosthetic device, and component parts thereof including lead wires and abandoned leads.

The AIMD external telemetry programmer electromagnetic signal is typically transmitted in the LF or HF frequency range.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a perspective and somewhat schematic view of a prior art active implantable medical device (AIMD) including an implanted lead directed to the heart of a patient;

FIG. 11 illustrates a bipolar cardiac pacemaker lead showing the distal tip and the distal ring electrodes;

FIG. 12 is an enlarged, fragmented schematic illustration of the area illustrated by the line 12-12 in FIG. 11 with an L-C bandstop filter shown in series with both the distal tip and the ring electrodes;

DETAILED DESCRIPTION OF THE PREFERRED EMBODIMENTS

Figure 1:
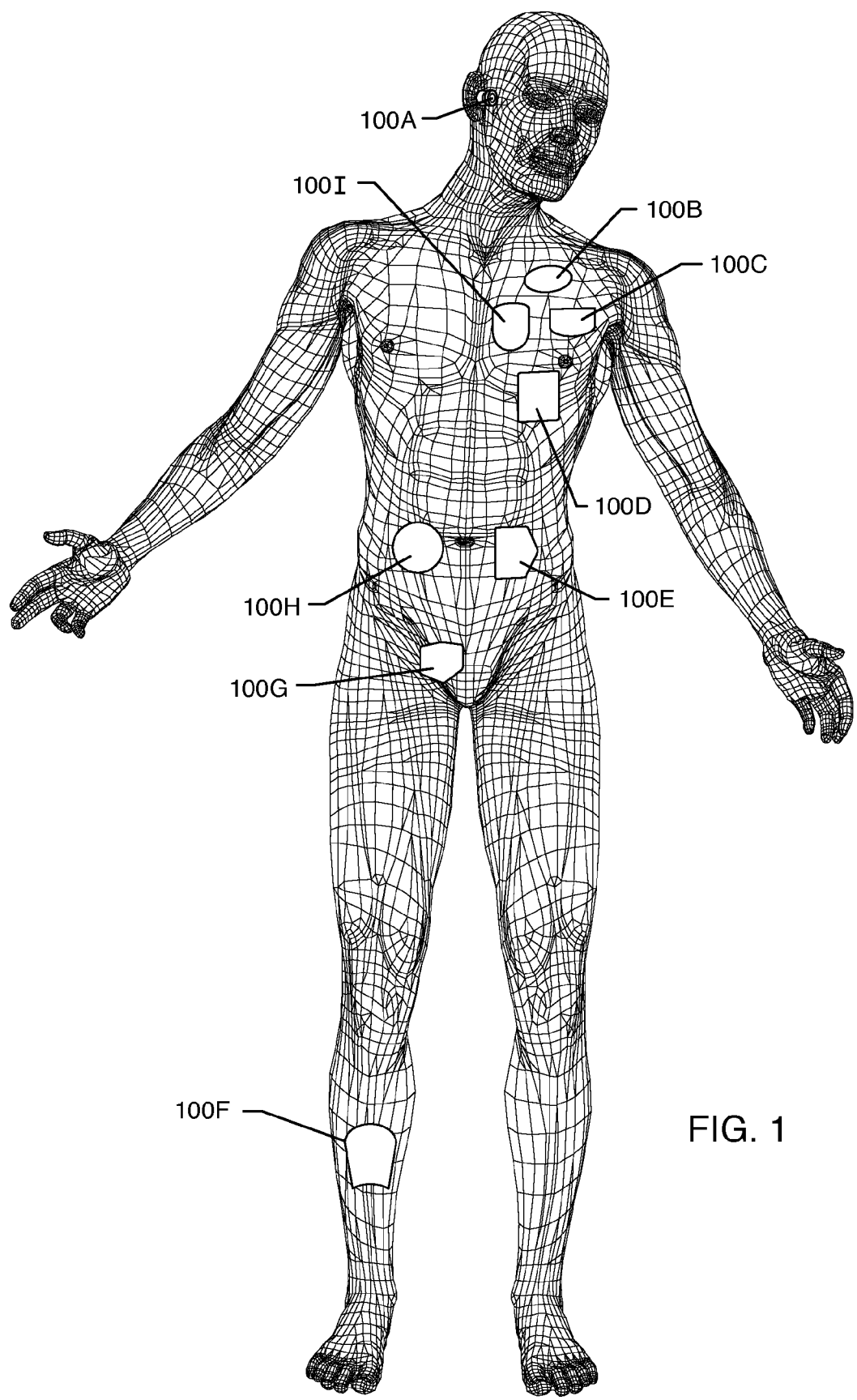
FIG. 1 is a wire-formed diagram of a generic human body showing a number of active implantable medical devices (AIMDs.

As shown in the drawings, for purposes of illustration, the present invention pertains to RFID identification of information regarding MRI compatibility including inductors, bandstop filters, or energy dissipating surfaces associated with implanted leads of active medical devices to protect the patient and/or medical device from undesirable or excessive RF induced currents, such as those generated during MRI and other medical procedures. The present invention resides in the design of AIMD external telemetry programmers that are enabled to have RFID interrogate and read capabilities. In one embodiment, the AIMD external telemetry programmer may also have read/write capabilities. An implantable RFID tag is associated with either the patient, an AIMD, an implanted lead, or an abandoned lead.

In the following description, functionally equivalent elements shown in various embodiments will often be referred to utilizing the same reference number.

FIG. 1 illustrates various types of active implantable and external medical devices 100 that are currently in use. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. 100C shows a cardiac pacemaker which is well-known in the art. 100D includes the family of left ventricular assist devices (LVAD's) and artificial hearts. 100E includes an entire family of drug pumps which can be used for dispensing of insulin, chemotherapy drugs, pain medications and the like. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices.

Referring now to FIG. 2, a prior art active implantable medical device (AIMD) 100 is illustrated. In general, the AIMD 100 could, for example, be a cardiac pacemaker 100C which includes a titanium housing 102. The titanium housing is hermetically sealed, however there is a point where lead wires 104a-104d must ingress and egress the hermetic seal. This is accomplished by providing a hermetic terminal assembly 106. Hermetic terminal assemblies are well known and generally consist of a ferrule 108 which is laser welded to the titanium housing 102 of the AIMD 100.

The IS1 connectors 110 that are designed to plug into the AIMD header block 112 are low voltage (pacemaker) connectors covered by an ANSI/AAMI standard IS-1. Higher voltage devices, such as implantable cardioverter defibrillators (ICDs), are covered by a standard known as the ANSI/AAMI DF-1. A new standard which integrates both high voltage and low voltage connectors into a new miniature connector series known as the IS-4 series. These connectors are typically routed in a pacemaker application endocardially down into the right ventricle and right atrium of the heart 114. It will be apparent to those skilled in the art that all of the descriptions herein are equally applicable to other types of AIMDs. These include implantable cardioverter defibrillators (using the aforementioned DF-1 connectors), neurostimulators (including deep brain stimulators, spinal cord stimulators, cochlear implants, incontinence stimulators and the like), and drug pumps. The present invention is also applicable to a wide variety of minimally invasive AIMDs. For example, in certain hospital catheter lab procedures, one can insert an AIMD for temporary use such as an ICD. Ventricular assist devices also can fall into this category. This list is not meant to be limiting, but is only exemplary of the applications of the novel technology currently described herein.

Figure 3:
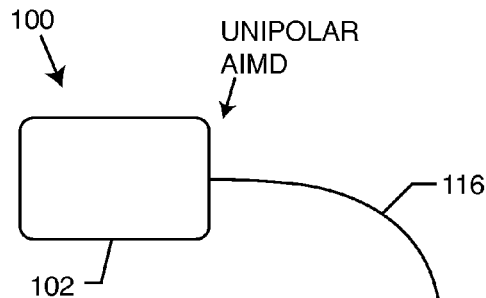
FIG. 3 is a schematic diagram of a unipolar active implantable medical device.

FIG. 3 is a general diagram of a unipolar active implantable medical device system 100. The housing 102 of the active implantable medical device 100 is typically titanium, stainless steel or the like, and acts as one conductive electrode. Inside of the AIMD hermetically sealed housing 102 are the AIMD electronics. Usually AIMDs include a battery, but that is not always the case. For example, a Bion may receive its energy from an external pulsing magnetic field. A lead 116 is routed in insulative relationship with the AIMD housing to an electrode 118 where is in contact with body tissue. In the case of a spinal cord stimulator 100H, the distal Tip 118 could be in the spinal cord. In the case of a deep brain stimulator 100I, the distal electrode 118 would be placed deep into the brain tissue, etc. In the case of a cardiac pacemaker 100C, the unipolar distal electrode 118 would typically be placed endocardially in a cardiac chamber. The lead 116 and electrode 118 can also be placed epicardially on the outside of the heart.

Figure 4:
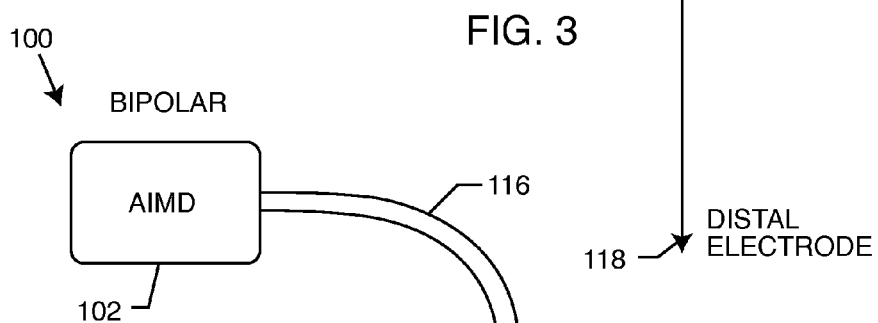
FIG. 4 is a diagram similar to FIG. 3, illustrating a bipolar AIMD system.

FIG. 4 is very similar to FIG. 3 except that it is a bipolar system (similar to that shown in FIG. 2). In this case, the return path is between the two distal electrodes 118 and 120. In the case of a cardiac pacemaker 100C, one of the electrodes is known as the distal Tip 118 and the other electrode which would float in the blood pool is known as the Ring 120 (see FIG. 5). In contrast, the return path in FIG. 3 is between the distal electrode 118 through body tissue to the conductive housing 102 of the implantable medical device 100.

Figure 5:
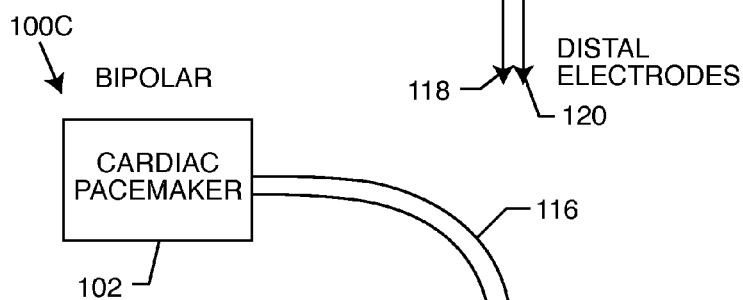
FIG. 5 is a diagram similar to FIGS. 3 and 4, illustrating a bipolar lead system with a distal tip and ring, typically used in a cardiac pacemaker.

FIG. 5 further illustrates a bipolar lead system with a distal Tip 118 and Ring 120 typically as used in a cardiac pacemaker 100C. In all of these applications, the patient could be exposed to the fields of an MRI scanner or other powerful emitter used during a medical diagnostic procedure. RF currents that are directly induced in the lead system 116 can cause heating by Ohmic ($I^2R$) losses in the lead system or by heating caused by RF current flowing from an electrode into body tissue. If these currents become excessive, the associated heating can cause damage or even destructive ablation to body tissue.

Figure 6:
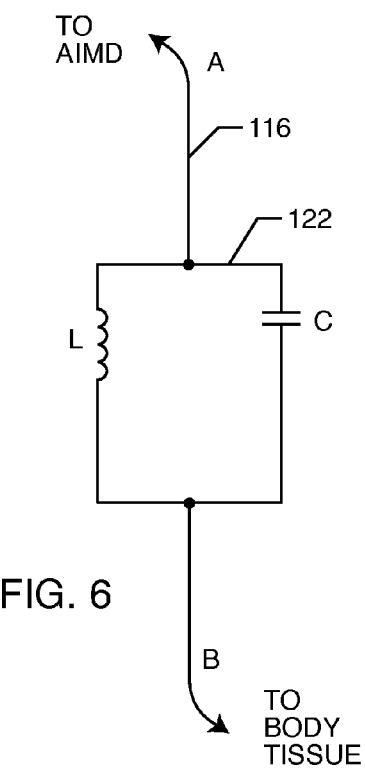
FIG. 6 is a schematic diagram showing a parallel combination of an inductor L and a capacitor C forming a bandstop filter placed in the lead systems of FIGS. 3-5.

FIG. 6 is a schematic diagram showing an ideal parallel combination of an inductor L and a capacitor C to be placed in the lead systems 116 previously described. This combination forms an ideal parallel bandstop circuit filter 122 which will resonate at a particular frequency ($f_r$). (Ideal means that resistive losses have been omitted from the model for simplicity).

It is important to note the certain lead systems are evolving to be compatible with specific types of medical diagnostic procedures. Or example, US 2007-0112398 A1 and US 2006-0247684 A1, both of which are incorporated herein by reference, disclose the use of bandstop filters placed in series with leads or circuits of active implantable medical devices to enhance their MRI compatibility.

In addition to bandstop filters, there are many other methods being developed to make implantable lead systems compatible with specific types of MRI equipment. For example, see U.S. Pat. No. 7,751,903, the contents of which are incorporated herein by reference, which discloses energy dissipating surfaces associated with implanted leads. There are also other methods under development to make implantable leads compatible with MRI systems. These other methods include controlling the resonant length of implanted leads (to a specific fraction of the MRI RF frequency wavelength), controlling lead winding pitch or coiling factors, placing inductors along the length of the lead, etc. The RFID-enabled external AIMD telemetry programmer in coordination with an RFID tag that's associated with the implanted lead can identify the MRI compatibility of any AIMD, external medical device and/or its associated implanted lead system.

There is also a significant issue related to abandoned leads. Often leads are abandoned for various reasons, such as an increase in pacing capture threshold, a decrease in insulation resistance, or the like. It has been shown in the literature that abandoned leads are particularly dangerous during MRI diagnostic procedures. Abandoned leads tend to overheat because there is no other place for induced energy to go than through the distal electrode into surrounding tissues. For more information on abandoned leads and methods of terminating them, refer to US 2010/0174349, the contents of which are incorporated herein by reference. Accordingly, the present invention is applicable to leads connected to active implantable medical devices, implanted leads connected to external medical devices, and also to abandoned leads.

Figure 7:
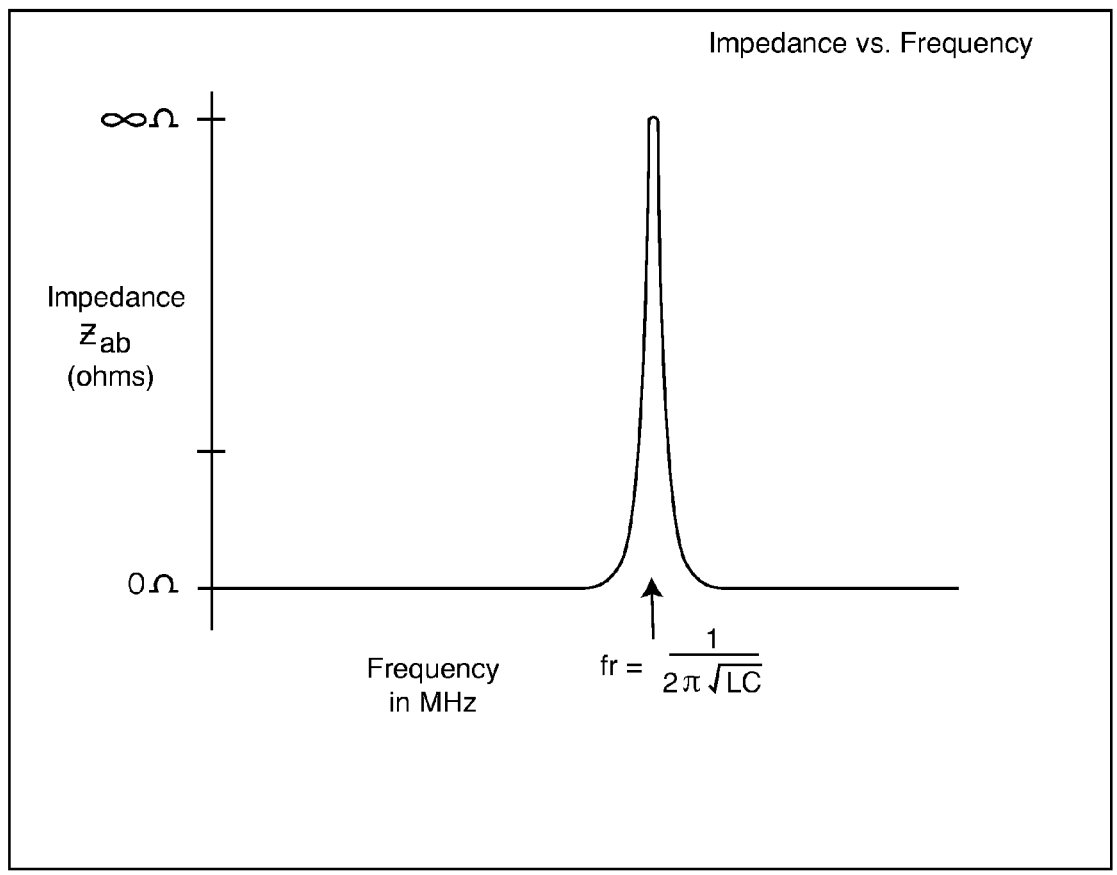
FIG. 7 is a graph showing impedance versus frequency for the ideal bandstop filter circuit of FIG. 6.

FIG. 7 gives the frequency of resonance $f_r$ for the parallel L-C bandstop circuit 122 of FIG. 6: where $f_r$ is the frequency of resonance in Hertz, L is the inductance in Henries and C is the capacitance in Farads. Clinical MRI systems vary in static field strength from 0.5 Tesla all the way up to 3 Tesla with newer research machines going as high as 11.4 T. The frequency of the pulsed RF field associated with the static field is given by the Lamour Equation, $f=\gamma_H T$, where T is the field strength in Teslas, and γ is gyromagnetic ratio for hydrogen, which is 42.58 MHz/T. Accordingly, a 3 Tesla MRI system has a pulsed RF field of approximately 128 MHz.

The resonant frequency fr of an ideal bandstop filter can be predicted by using the equation:

$$f_r = \frac{1}{2\pi\sqrt{LC}},$$

Where $f_r$ is the resonant frequency, L is the inductance, in Henries, of the inductor component, and C is the capacitance, in Farads, of the capacitor component. In this equation, there are three variables: $f_r$, L, and C. The resonant frequency, $f_r$, is a function of the MRI system of interest. As previously discussed, a 1.5 T MRI system utilizes an RF system operating at approximately 64 MHz, a 3.0 T system utilizes a 128 MHz RF, and so on. By determining the MRI system of interest, only L and C remain. By artificially setting one of these parameters, a filter designer needs only to solve for the remaining variable.

This equation, however, only deals with ideal inductor and capacitor elements. Real inductor and capacitor components include series resistive elements, which are represented by the circuit diagram in FIG. 8. These resistive components are due to material and design considerations, and are not necessarily independent of the respective inductive and capacitive values of the components.

Figure 8:
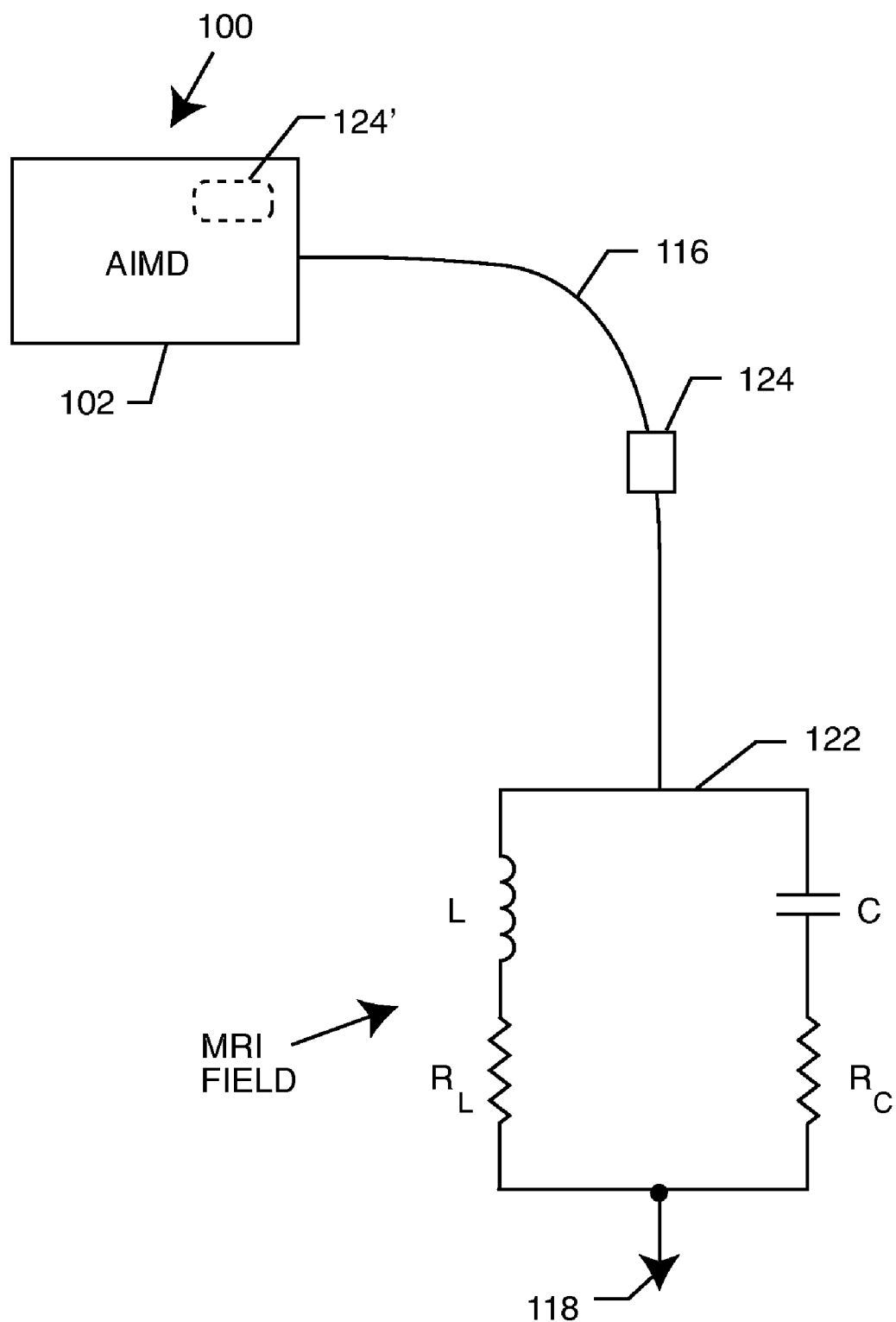
FIG. 8 is a diagram similar to FIG. 3, illustrating the bandstop filter circuit added near a unipolar distal electrode of an AIMD, wherein the bandstop filter includes resistive loss elements to control Q.

By modeling the resistive elements with the reactive elements in a circuit modeling program such as P-Spice, one can see that the $R_L$ and $R_C$, as shown in FIG. 8, provide a significant contribution. As the total real resistance in the circuit increases, the 3 dB bandwidth of the bandstop filter widens. This is a desired effect in this invention, since the widened 3 dB bandwidth corresponds to a broader range of filtered frequencies. For example, an 'ideal' bandstop filter would resonate at only 64 MHz (for a 1.5 T MRI), and have little to no attenuation effect at 3.0 T MRI (128 MHz). However, a bandstop filter with a real resistive contribution would display a significant increase in the 3 dB bandwidth, and if a designer chose appropriate components, the bandstop filter could provide filtering over a range of MRI pulsed RF frequencies.

An increase in bandstop filter attenuation does not come without performance drawbacks. Since the energy dissipated by the bandstop is finite, broadening the bandwidth of the bandstop filter 122 also has the effect of depressing the maximum attenuation of the circuit at resonance. If the attenuation drops too low, filtering performance at MRI RF pulse frequency can be negatively affected.

In the preferred methodology, a relatively high inductance should be chosen (>100 nH). The selectivity of the bandstop filter is determined by the ratio of L/C. Accordingly, too low of an inductance value will not provide the proper amount of attenuation or the proper 3 dB bandwidth at the selected MRI pulsed frequency. However, a relatively low series resistance is required of the inductor to guarantee low attenuation at lower frequencies. Since the series resistance in an inductor is a function of the material properties and the design geometry, careful component selection becomes critical.

FIG. 7 is a graph showing impedance versus frequency for the ideal parallel bandstop circuit 122 of FIG. 6. As one can see, using ideal (zero resistance) circuit components, the impedance measured between points A and B for the parallel bandstop circuit 122 shown in FIG. 6 is zero until one approaches the resonant frequency $f_r$. At the frequency of resonance, these ideal components combine together to approach an infinite impedance. This means that at one selected RF frequency, the impedance between points A and B in FIG. 6 will appear very high (analogous to opening a switch). Accordingly, it would be possible, for example, in the case of a cardiac pacemaker, to design the cardiac pacemaker for compatibility with one single popular MRI system. The problem is, for 1.5 or 3 Tesla labeled and marketed scanners, not all the RF pulse frequencies are the same. For example, 1.5 Tesla scanners vary somewhat in their static magnetic field strengths (they're not all exactly 1.5 Tesla). The RF pulse frequencies given by the Lamour equation is 42.56 times the static magnetic field strength (for hydrogen scanners). When one surveys all the various manufacturers of 1.5 Tesla scanners, one will find that not only does the static magnetic field strength vary somewhat, but the RF pulse frequencies differ from one another by as much as 0.5 MHz. Referring once again to FIG. 7, an ideal bandstop filter 122 might work for a single model and single manufacturer of one of these systems, but it would be too narrow in bandwidth to work for the range of commercially available 1.5 Tesla scanners.

FIG. 8 is a schematic drawing of the parallel bandstop circuit 122 of FIG. 6, except in this case the inductor L and the capacitor C are not ideal. That is, the capacitor C has its own internal resistance $R_C$, which is otherwise known in the industry as dissipation factor or equivalent series resistance (ESR). The inductor L also has a resistance $R_L$. The resistance $R_L$ and resistance $R_C$ shown in FIG. 8 could also be from discrete resistors such as chip resistors.

Again, FIG. 8 is a drawing of the unipolar AIMD lead wire system, previously shown in FIG. 3, with the bandstop filter 122 added near the distal electrode 118. The presence of the bandstop filter 122 will present a very high impedance at one or more specific MRI RF pulse frequencies. This will prevent currents from circulating through the distal electrode 118 into body tissue at this selected frequency(s). This will provide a very high degree of important protection to the patient so that distal TIP heating does not cause tissue damage.

Figure 18:
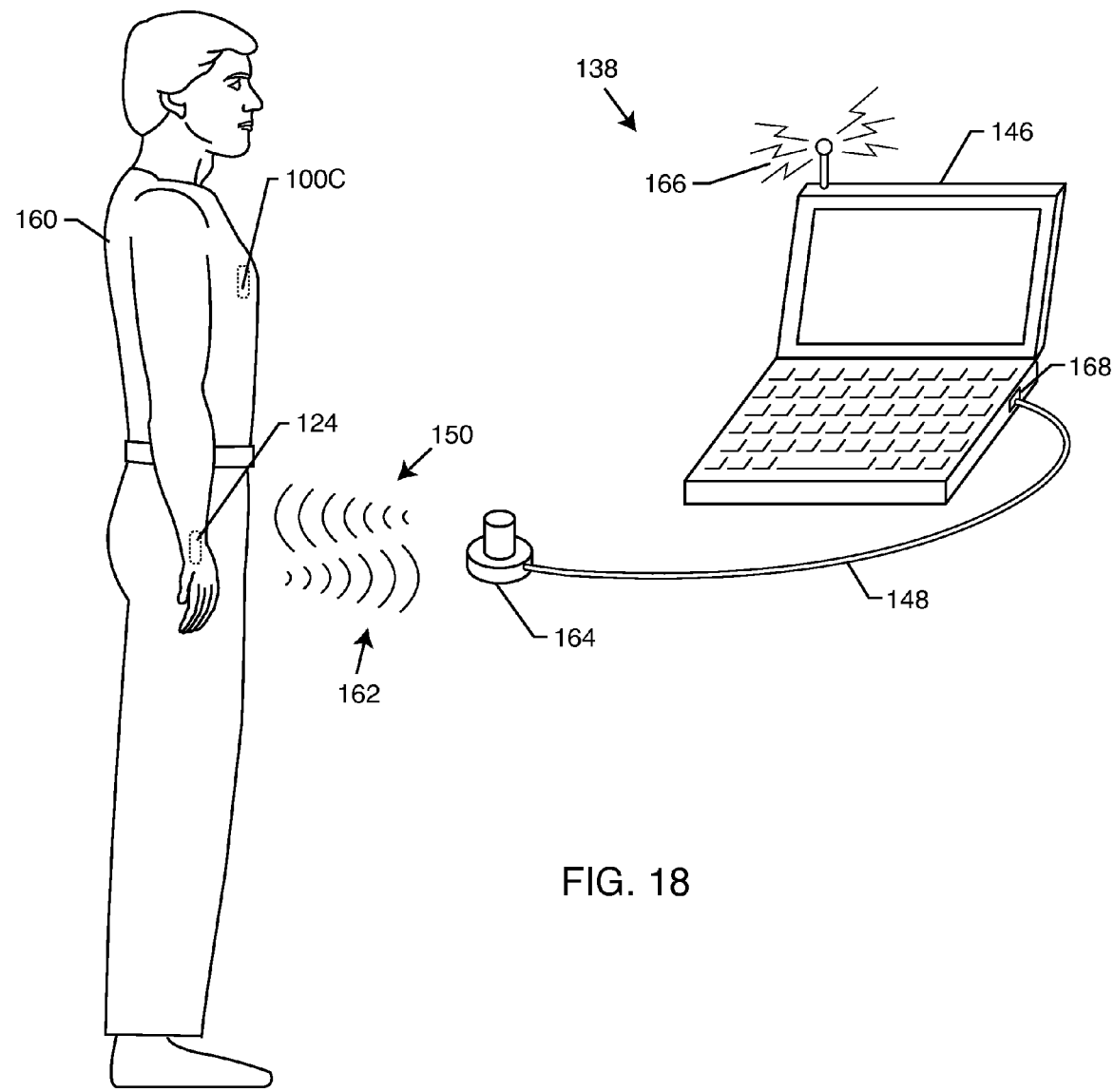
FIG. 18 is similar to FIG. 17, wherein an antenna is attached by cable to the AIMD external telemetry programmer.

In FIG. 8, one can see that an optional RFID tag 124 has been placed on or in the lead 116. The RFID tag 124 could also be placed on or in the AIMD 100 as shown at 124'. Another alternative would be to place the RFID tag at some other location within the patient's body, such as the patient's wrist (FIG. 18). US 2006/0212096 A1, the contents of which are incorporated herein, describes how to place RFID tags and hermetically seal them in the header block of a cardiac pacemaker or the like. The RFID tag may also be externally worn such as in a patient's wallet in the form of a patient ID card, an RFID tag bracelet, an RFID tag necklace or the like.

It is common in the art that "mix and match" goes on between the implantable medical device and the implanted lead systems. This is particularly true for cardiac pacemakers. For example, it is very common that a St. Jude pacemaker could be used with Medtronic leads and vice versa. It is also common that leads will stay implanted in the human body much longer than the actual active implantable medical device. For example, a pacemaker patient may have leads implanted for forty years or longer where the pacemaker itself is replaced in the pectoral pocket and plugged into existing leads every five to seven years. The bandstop filter is designed to work with many model pacemakers to prevent overheating during MRI procedures of the lead and it's associated distal Tip. Accordingly, it is very important over time that a hospital or MRI lab be able to identify which patients have MRI compatible AIMD and associated lead systems and which do not.

It is a feature of the present invention that an RFID tag 124 can be affixed to or placed adjacent to an implantable device or in the lead system, or both, so that system MRI compatibility can be appropriately identified. The RFID tag 124 could also include important information such as the resonant frequency that the distal TIP bandstop was designed for. For example, the RFID tag 124 could emit a pulse indicating that it is RFID compatible at 1.5 T (64 MHz). It is important that the active implantable medical device 100 also incorporate robust EMI filters such that the RFID emitter (reader or scanner) not interfere with the electronics of the AIMD itself. An ideal RFID frequency for the present invention would be 13.56 MHz or lower which would readily penetrate body tissue and be detected by the RFID tag 124 that is attached to the lead 116. There are a variety of fixation methods that can be used to attach the RFID tag 124 to the lead, including bonding within the encapsulation material of the lead itself or by using a tie or suture attachment. It is not even necessary that the RFID tag 124 be directly attached to the leads themselves. For example, it is also known in the art that RFID tags can be injected anywhere in the human body, for example, near the wrist. The RFID tag could also be worn externally or carried as in a wallet RFID patient ID card. In this case, the RFID tag 124 would include important information about the presence and MRI compatibility of the lead wire system and/or the AIMD itself.

Figure 9:
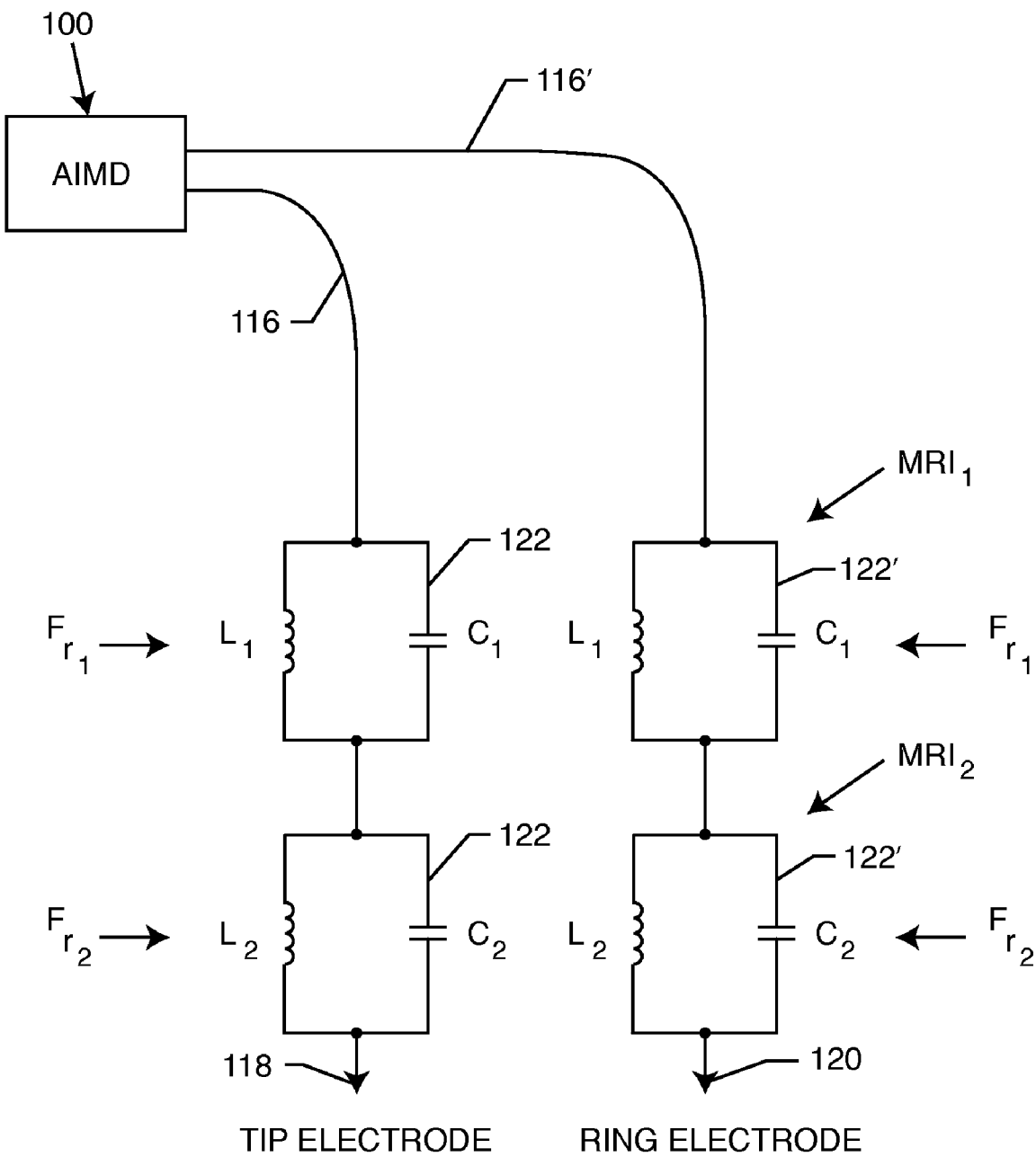
FIG. 9 is a diagram similar to FIGS. 4 and 8, redrawn to show multiple bandstop filters in bipolar lead electrodes.

FIG. 9 is the bipolar system of FIG. 4 redrawn to show two bandstop filters 122, 122' in each lead 116, 116'. In this case, there is a bandstop circuit $F_{r1}$ consisting of $L_1$ and $C_1$ in both of the bipolar lead wires 116, 116', which is designed to resonate at one selected frequency. For a 1.5 Tesla MRI system, this would be 64 MHz. These are then placed in series with a second set of bandstop filters which are designed to resonate at $F_{r2}$. These consist of $L_2$, $C_2$ parallel inductor capacitor combinations. These could be designed for operation in a 3 Tesla MRI system and would therefore be designed to resonate at 128 MHz. In this way, currents would be blocked from both types of MRI systems. A single RFID tag 124 could be associated with either lead 116, 116' or anywhere in or on the patient, so as to identify both of the leads as incorporating bandstop filters 122, 122'.

Figure 10:
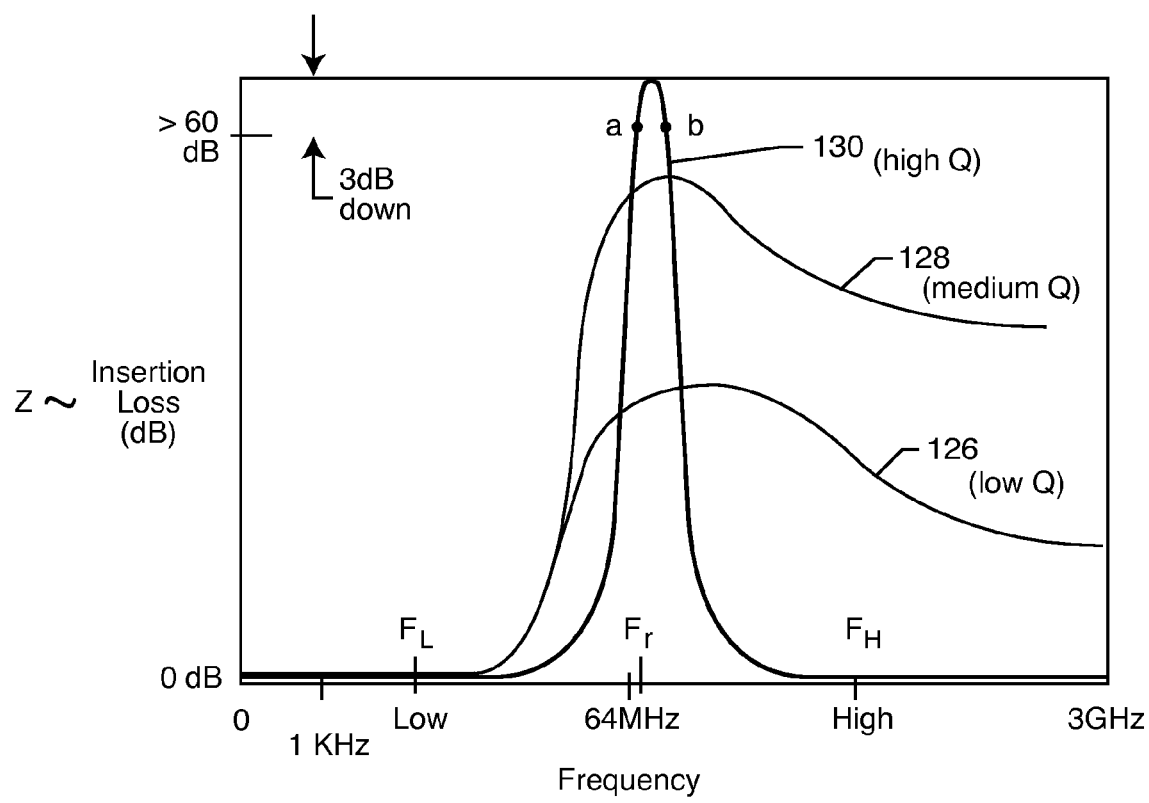
FIG. 10 is a graph of insertion loss verses frequency for bandstop filters having differing quality "Q" factors.

Efficiency of the overall bandstop circuit 122 is also measured in terms of a quality factor, Q, although this factor is defined differently than the one previously mentioned for discrete capacitors and inductors. The circuit Q is typically expressed using the following equation:

$$Q = \frac{f_r}{\Delta f_{3dB}}$$

Where $f_r$ is the resonance frequency, and $\Delta f_{3dB}$ shown as points a and b in FIG. 10, is the bandwidth of the bandstop filter 122. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values result in a narrower 3 dB bandwidth.

Material and application parameters must be taken into consideration when designing bandstop filters. Most capacitor dielectric materials age 1%-5% in capacitance values per decade of time elapsed, which can result in a shift of the resonance frequency of upwards of 2.5%. In a high-Q filter, this could result in a significant and detrimental drop in bandstop performance. A low-Q filter would minimize the effects of resonance shift and would allow a wider frequency band through the filter. However, low Q filters also display lower than desirable attenuation behavior at the desired bandstop frequency (see FIG. 10, curve 126). For this reason, the optimum Q for the bandstop filter will embody inductor L and capacitor C resistive losses which will result in a medium Q bandstop filter as shown in curve 128 of FIG. 10.

The "Q" or quality factor of the bandstop circuit is very important. As mentioned, it is desirable to have a very low loss circuit at low frequencies such that the biological signals not be undesirably attenuated. The quality factor not only determines the loss of the filter, but also affects its 3 dB bandwidth. If one does a plot of the filter response curve (Bode plot), the 3 dB bandwidth determines how sharply the filter will rise and fall. With reference to curve 130 of FIG. 10, for a bandstop filter that is resonant at 128 MHz, an ideal response would be one that had infinite attenuation at 128 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one. This is particularly true when one also considers that the bandstop filter circuit must also be miniature, highly reliable, and completely biocompatible.

The performance of the circuit is directly related to the efficiency of both the inductor and the capacitor; the less efficient each component is, the more heat loss that results, and this can be expressed by the addition of resistor elements to the ideal circuit diagram. The effect of lower Q in the bandstop circuit is to broaden the resonance peak about the resonance frequency. By deliberately using a lower Q inductor, one can broaden the resonance such that relatively high impedance (high attenuation) is presented at multiple MRI RF frequencies, for the full 0.5 MHz range of commercially available 1.5 Tesla scanners.

Referring again to FIG. 10, one can see curve 128 wherein a high Q inductor has been used in combination with a low Q capacitor. This also has a very desirable effect in that at very low frequencies, the impedance of the bandstop circuit 122 is essentially zero (below 1 ohm) ohms (or zero dB loss). This means that biologic frequencies are not undesirably attenuated. However, one can see that the 3 db bandwidth is much larger. This is desirable as it will block multiple RF frequencies. As one goes even higher in frequency, curve 164 will desirably attenuate other high frequency EMI signals, such as those from cellular telephones, microwave ovens and the like. Accordingly, it is often desirable that medium resistive loss inductors be used in combination with relatively low loss capacitors to achieve a medium or lower Q bandstop filter.

Again referring to FIG. 10, one can see that if the Q of the overall circuit or of the individual components becomes too low, then we have a serious degradation in the overall attenuation of the bandstop filter. Accordingly, a careful balance between component design and bandstop circuit Q must be achieved.

FIG. 11 illustrates a single chamber bipolar cardiac pacemaker 100C and its leads 116, 116' showing the distal Tip 118 and the distal Ring 120 electrodes. This is a spiral wound (coaxial) system where the Ring coil 116' is wrapped around the Tip coil 116. There are other types of pacemaker lead systems in which these two leads lay parallel to one another (known as a bifilar lead system).

FIG. 12 is a schematic illustration of the area 12-12 in FIG. 11. In the area of the distal Tip 118 and Ring 120 electrodes, bandstop filters 122 and 122' have been placed in series with each of the respective Tip and Ring circuits. The Ring circuit wire 116' has been drawn straight instead of coiled for simplicity. Accordingly, at an MRI pulsed RF frequency, a high impedance will be presented thereby reducing or stopping the flow of undesirable MRI induced RF current.

The pacemaker Tip 118 is designed to be inserted into intimate contact with myocardial (endocardial) tissue. Over time it becomes encapsulated and fully embedded or buried within such tissue. However, the Ring 120 is designed to float within the blood pool, for example, in the ventricle or atrium. With the constant blood perfusion, the Ring 120 is somewhat cooled during medical diagnostic procedures, such as MRI. However, the Tip 118 which is embedded in the myocardial tissue, is thermally insulated in comparison. It can't always be assumed that a Ring electrode 120 that is floating in the blood pool will be adequately cooled by the flow of blood. There are certain types of patients that have illnesses that lead to very low blood flow rates and perfusion issues. Accordingly, in a preferred embodiment both the distal Tip and the Ring would incorporate bandstop filters 122, 122'. Accordingly, the operation of the bandstop filter 122 is more important in the Tip 118 than it is in the Ring 120 in order to prevent distal Tip heating and associated tissue damage. In most cardiac applications, only a Tip bandstop filter 122 is required for MRI compatibility.

Figure 13:
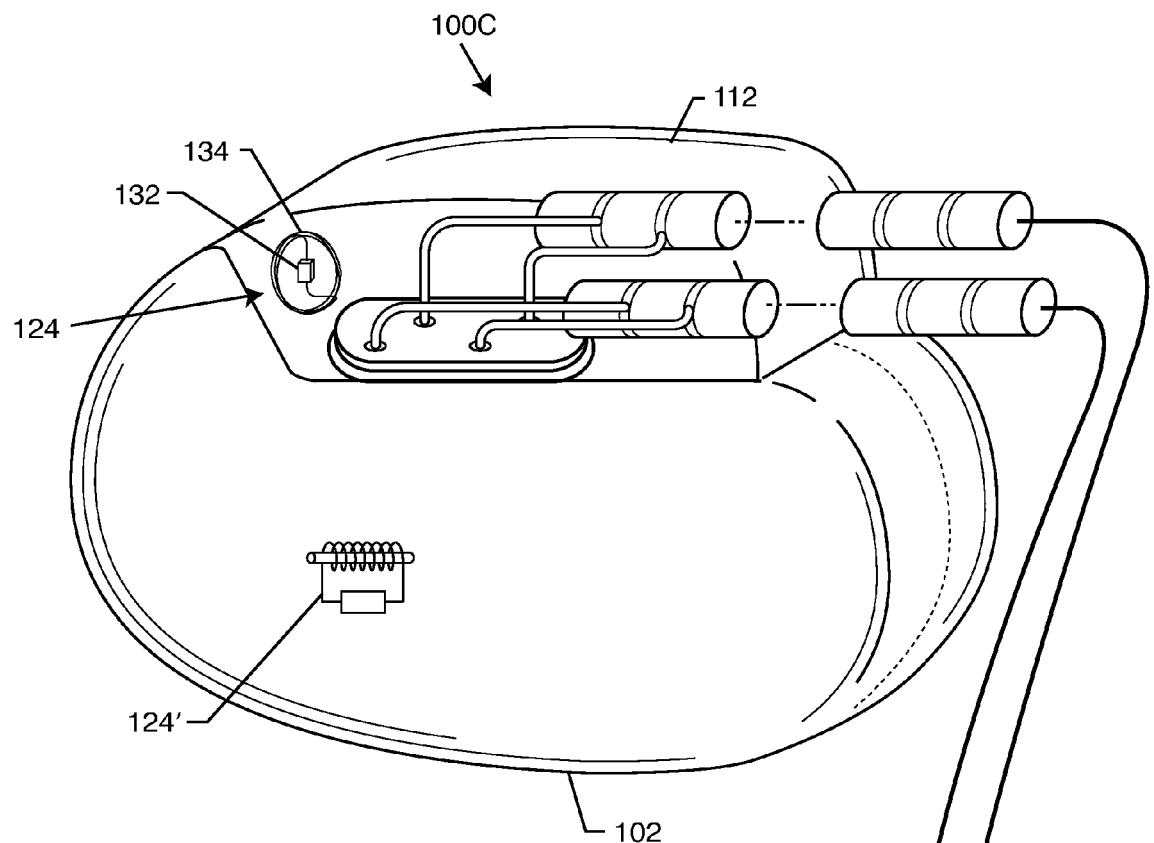
FIG. 13 shows a prior art cardiac pacemaker that includes an RFID tag and its associated antenna.

FIG. 13 illustrates a prior art cardiac pacemaker 100C which has an RFID chip 132 and its associated antenna 134 in its polymer header block 112. The RFID chip plus its antenna are known in the art as an RFID tag 124. There are many other possible locations for the RFID tag 124 other than in the pacemaker header block 112 as shown. The RFID tag 124' could be disposed inside of the AIMD housing 102, or the RFID tag could be surgically implanted or surgically injected anywhere in the human body. The tag could also be externally carried or worn by the patient.

Figure 14:
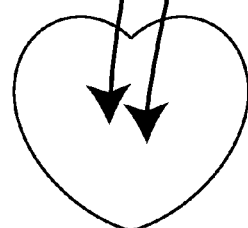
FIG. 14 illustrates an RFID tag associated with an implanted lead.
Figure 14:
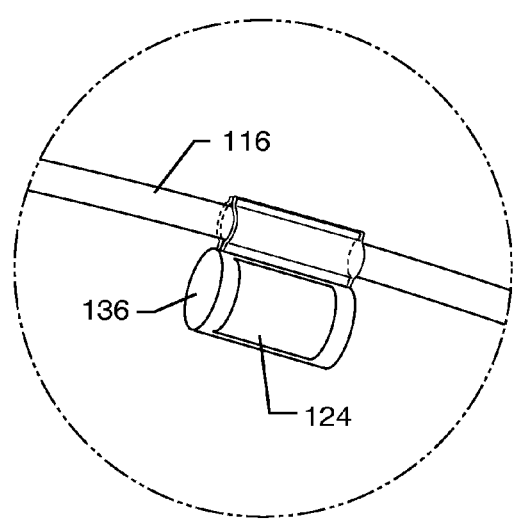

FIG. 14 illustrates an implanted lead 116 with an RFID tag 124 which includes an RFID chip and antenna attached in a package 136. As previously discussed, it is equally important to know the MRI compatibility of an AIMD and also its implanted leads.

Figure 15:
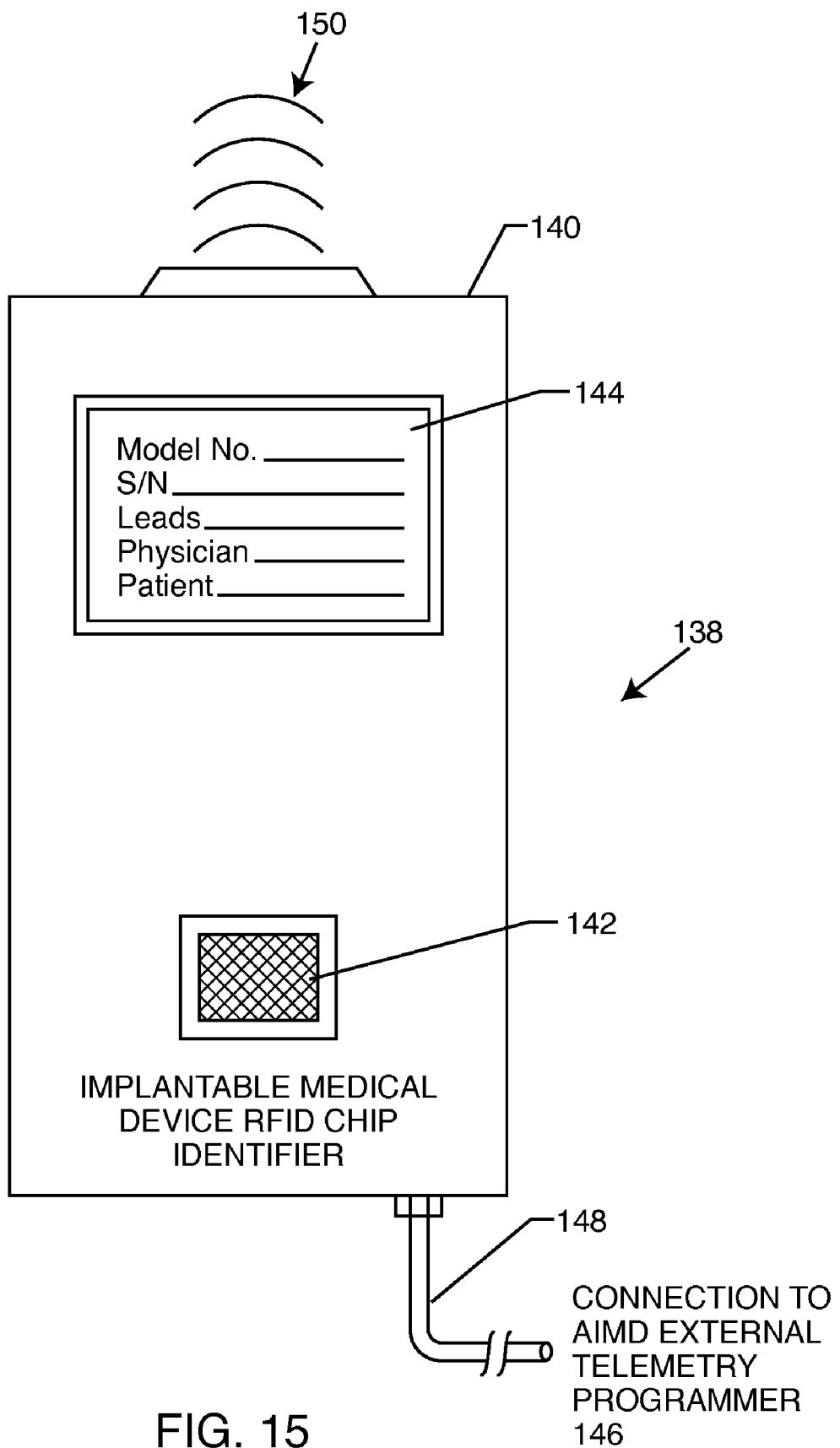
FIG. 15 is a schematic illustration of a novel RFID communicator system embodying the present invention.

FIG. 15 is the top view of a novel hand-held RFID reader/communicator 138 system of the present invention which is connected to an AIMD external telemetry programmer (not shown). Shown is a hand-held RFID interrogator 140 push button switch 142 and a display 144, which could display medical device model number, serial number, type and model number of leads, name and contact information for implanting physician, name and other pertinent information about the patient (with informed patient consent). Since the hand-held interrogator 140 is connected to either a newly designed or prior art AIMD external telemetry programmer 146, the display of medical device model number, serial number and the like need not be on the hand-held unit 140 as shown. Cable 148 is connected to an AIMD external programmer 146, with appropriate software modifications. The external telemetry programmer 146 could also display the information illustrated in window 144 of FIG. 15. It would also be possible to eliminate the push button 142 shown in FIG. 15 and instead use the keyboard of the external telemetry programmer 146 to initiate RFID interrogation. The combination of the handheld RFID interrogator 140 and its connection 148 to an external AIMD telemetry programmer 146 forms an RFID reader/communicator system 138 of the present invention. The transmit pulses 150 are shown as a series of electromagnetic waves being emanated from the RFID communicator 138. The communicator 138 is integrated into or connected to an AIMD external telemetry programmer which may include a printer, printer interface or computer/network connection for creating a permanent record. This would be advantageous for medical personnel at the scene, for creating accurate medical records and for future reference in case of medical, legal or other delayed concerns. The RFID reader of the present invention need not be hand-held as shown in FIG. 15, but it could be integrated wholly or partially into the AIMD external telemetry programmer itself.

Figure 16:
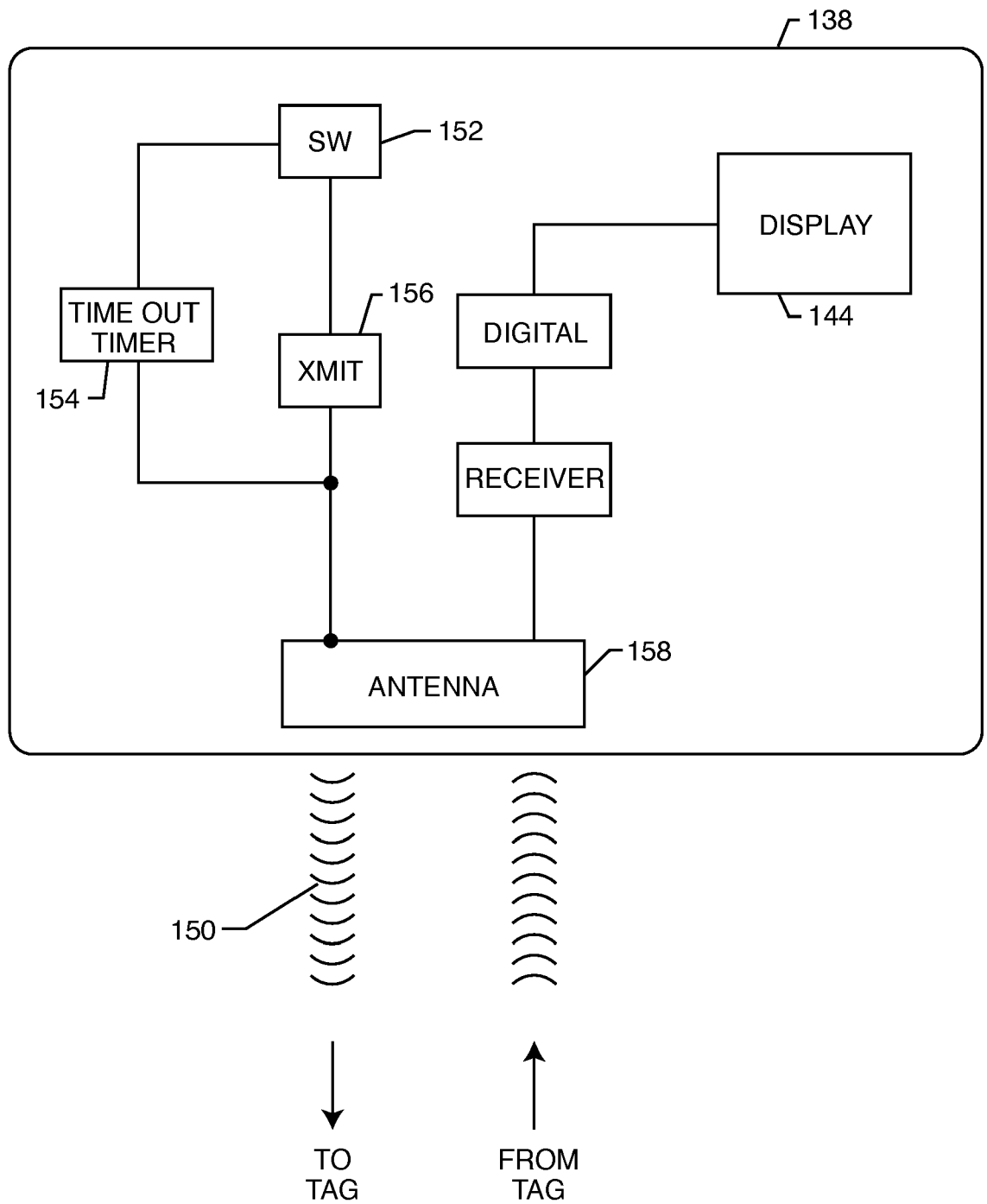
FIG. 16 is a functional block diagram showing a novel limited RFID transmit time and time out application of the present invention.

FIG. 16 is a functional block diagram showing a novel optional application of the present invention. Shown is the switch SW (152), which can be, but is not limited to, a push button switch like that shown in FIG. 15. In this case, the switch SW (152) would contain special electronic circuitry so it could transmit an electronic pulse 150 for no longer than 5 seconds, or other physiologically safe duration. In a preferred embodiment, the electromagnetic pulse 150 could have a duration or maximum transmit time of no longer than 0.5 seconds combined with a time-out period of 2 seconds or more. Depending on the type of patient AIMD, the transmit time can vary from nanoseconds to several minutes.

The concept of an RFID interrogator with a limited transmit time and a time-out period is more thoroughly described in US 2010/0123547, the contents of which are incorporated herein by reference.

For example, for cardiac pacemaker, limiting transmit time to 0.5 seconds, would, by definition, make it impossible to have a prolonged inhibition type response from an implanted cardiac pacemaker or implanted defibrillator. Dropping of a few paced beats would not be detected by the patient and regardless, would be of no clinical significance. This approach provides an even greater safety margin for ICD compared with bradycardia pacing patient requirements as when implantable defibrillators sense rapid signals that could represent a dangerous ventricular arrhythmia, they begin to charge a high-energy storage capacitor. A final interrogation (sensing of biological signals) is made prior to delivery of the high voltage shock. This entire process takes at least 5 seconds and a progressively longer time as the ICD battery ages. Accordingly, by limiting the transmit pulse of the RFID-enabled AIMD external telemetry programmer to less than 5 seconds (preferably less than 500 milliseconds), one is guaranteed that no harm can come to the patient from malfunction or inhibition of a pacemaker or an implantable defibrillator, during transmission of important diagnostic information.

A similar corollary is made for all other types of neurostimulators. For example, consider the case of a cochlear implant. If one were to have a patient in an emergency room in a life threatening situation, the application of the reader of the present invention would only cause the patient to hear some audible buzzes during the short burst from the RFID reader. For example, for an epilepsy control stimulator, one or two extra pulses to the brain would be of no clinical significance. The same would be true of a spinal cord stimulator, a vagus cord stimulator, an incontinence (bladder control) stimulator, or the like. Even if the short RF burst from the reader transiently terminated the output of a pain control stimulator, the patient would be without pain suppression stimuli a maximum of only 5 seconds. Therefore, this feature is applicable to all types of active implantable medical devices and is not just limited to pacemakers and implantable defibrillators.

Referring once again to FIG. 16, one can see that there is a timer circuit 154 designed to bypass the RF signal generator 156 within the RFID reader 138. After the transmit pulse 150 is sent to the RFID tag 122 by antenna 158, which has been implanted inside a human or worn by a person in another RF signal sensitive location, the timer 154 prevents the switch 152 from working again for a predetermined amount of time, for example, at least 2 seconds. Therefore, if the push button switch SW (152) is held down continuously, only a single output sequence is delivered and a second and/or further outputs are suppressed until after the specified novel time-out or delay period(s) has occurred. No matter how long the switch 152 is activated and/or reactivated, the transmitter cannot continue to or continuously transmit an RF or any other type of electromagnetic signal. For example, applying this feature to cardiac rhythm management devices, an optimal delay or time-out period would be in the range of 2 seconds, giving the heart, for example, time to revert to its intrinsic stable rhythm before it could be disturbed again by additional dropped beats if the reader were to retransmit. Of course, in patients with pacing capable devices, but without pulse generator dependent rhythms, for example, during normal sinus rhythm, the reader transmissions would have no effect even when the switch was appropriately activated. On the other hand, in ICD patients, whether paced or in a normal intrinsic rhythm, there would also be potential risk during RF reader activation, in particular, as transmission durations reach and exceeded ten seconds.

Referring once again to FIG. 15, the RFID reader 138 or the external AIMD telemetry programmer has a transmit button 142 (which could even be a soft key). Even if the transmit button 142 is pressed repeatedly, if the transmit time is limited, e.g. to less than 0.5 seconds (500 milliseconds), then at most a pacemaker patient will only drop a few heart beats. However, the time-out circuit is equally important. If for some reason the transmit button 142 is pushed over and over again, this could cause a prolonged pacemaker inhibition period which could be potentially pro-arrhythmic or even life-threatening to the patient. The optional novel time-out circuit of the present invention ensures that the transmit button 142 will not work again for a specified period of time.

For pacemaker and implantable defibrillator applications, the ideal time-out period is based on a number of factors. For a cardiac pacemaker, that has to do with the wide range of human conditions and their particular underlying cardiovascular disease or cardiac hemodynamics. Taking all of this into consideration, the preferred transmit time is 500 milliseconds or less and the preferred time-out period is two seconds or longer. This embodiment is also ideal for implantable cardioverter defibrillators, which in order to deliver therapy, must first detect a dangerous (fast rate) ventricular arrhythmia. If such fast rate ventricular arrhythmia is detected, the ICD high energy internal storage capacitor is charged up. It typically takes several seconds for the battery to charge up the capacitor. Then the ICD reinterrogates to see if the dangerous arrhythmia is still present. If it is, the ICD delivers a high voltage shock. This entire process generally takes longer than 6 seconds.

In a preferred embodiment, the total transmit time of the electromagnetic signal would be limited to 500 milliseconds (0.5 seconds). This would be combined with a time-out period of 2 seconds or more. If one does the math over a full minute, this would mean that a pacemaker dependent patient that was being paced at 50 beats per minute would lose, at maximum, 10 beats over that full minute or have an effective 40 beats per minute heart rate. This would put the patient right on the edge of the indications for a cardiac pacemaker. However, this still provides a high degree of safety for an athletic patient, since it is well known that athletes can drop to as low as 25 beats per minute before they become dizzy. Accordingly, the preferred embodiment would be to limit the total transmit time to 500 milliseconds and the time-out period to a minimum of 2 seconds. This preferred embodiment also works well for ICD and neurostimulator patients.

However, this feature of the present invention does not limit the transmit time and time-out period to any specific number. The reason for this is there is great variability in the characteristics of AIMDs. For example, AIMDs are evolving over time. Pacemakers are evolving to have more functions and more lead-based sensors. Accordingly, their EMI characteristics could change over time necessitating that the total transmit time and/or the time-out period be adjusted over time or even deemed unnecessary. In addition, it's quite possible, if not likely, to interrogate with an RFID reader a pacemaker and in the same patient, then later interrogate, for example, a spinal cord stimulator. This is particularly true for low frequency (LF) RFID chips that may be embedded inside the AIMD housing. The read range of these RFID readers is typically from 2 to 6 inches maximum. This would place the RFID reader in very close proximity to the AIMD that had an RFID tag associated with it. Accordingly, one could conceive of a reader that was used only for interrogating pacemakers when it was closely held. In this case, it would have to have a more limited transmit time and perhaps a longer time-out period. On the other hand, if one were interrogating a spinal cord stimulator, the transmit time and time-out period would not be nearly as critical because the spinal cord stimulator is not a lifesaving device. In other words, if the patient experienced a few seconds of pain, this would be far preferable than having the heart stop.

The transmit time is, of course, also related to the amount of information that is desired to be either written or retrieved from a tag. Accordingly, in the simplest embodiment, a transmit period of only a few nanoseconds may suffice. This would work in combination with a look-up table that would be built within the reader. In this case, all of the implantable medical device, such as a cardiac pacemaker, would have to transmit would be a two-letter code. This two-letter code would ideally be tied to an Association for the Advancement of Medical Instrumentation (AAMI) standard or International Standards Organization (ISO) standards wherein the manufacturers look-up tables would be contained. For example, the code A1 could stand for St. Jude Medical. It would only take the tag a few nanoseconds to transmit the code A1. On the other hand, if it were desired that the tag transmit not only manufacture, but in addition, model number, serial number, date of manufacture, name of both the patient and implanting physician and so on, then the data transmission time would increase. Accordingly, in the present invention, the transmission time would be limited, in general, from 1 nanosecond all the way to 2 seconds, and the time-out period can be from a few nanoseconds to a number of minutes. As mentioned, this is very device specific as well. A drug pump will not respond nearly the same way as a cardiac pacemaker, for example.

Figure 17:
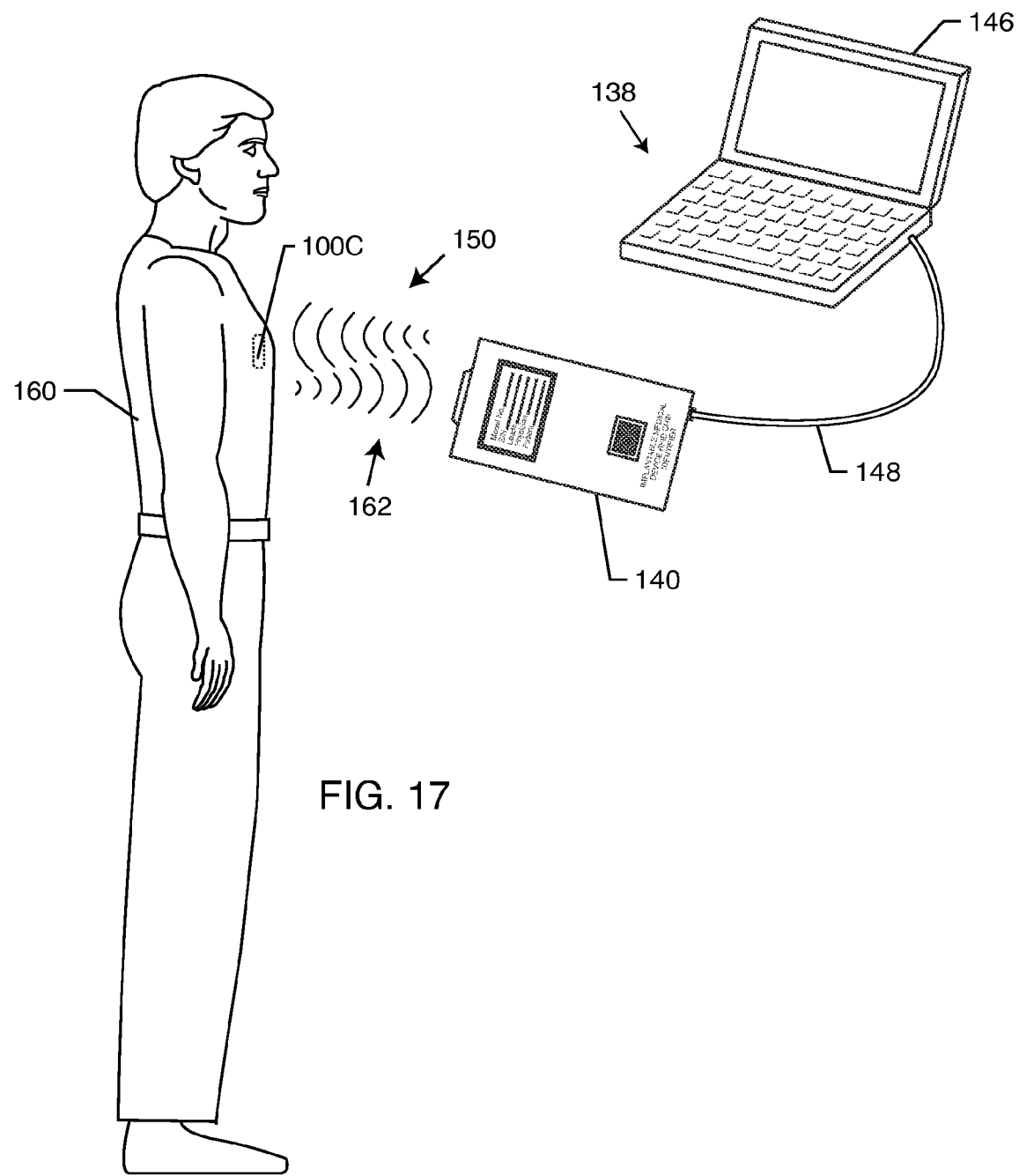
FIG. 17 is a depiction of a patient with an AIMD fitted with an RFID tag communicating with an RFID-enabled AIMD external telemetry programmer embodying the present invention.

FIG. 17 illustrates a patient 160 with an implanted pacemaker 100C. There is a great need in ambulances, hospital emergency rooms, and other environments to quickly and accurately detect the model number, the serial number and other information about any implanted medical device. This is also very important before certain diagnostic procedures such as MRI. Shown is the communicator unit 140 sending a signal 150 towards the implanted pacemaker 100C and its associated RFID tag (not shown). A return pulse 162 is emitted from the RFID tag which is received by the RFID communicator 140. This information, in turn, is transmitted via cable 148 to the external AIMD telemetry programmer 146. The RFID tag could also be implanted in other locations within the patient's body or even within a special patient ID card or wristband.

In summary, FIG. 17 illustrates yet another scenario in which RFID tags will soon be placed in AIMDs, and readers will deliberately be brought very close to the patient in order to identify information about the AIMD itself. The situation illustrated in FIG. 17 is probably the most dangerous for a pacemaker or ICD patient. In this example a very powerful RFID reader is deliberately placed literally right up against the patient's chest in order to retrieve information from the pacemaker or ICD itself. Obviously, it would be highly undesirable if EMI from the reader interrogation signal disrupted the proper operation of the AIMD. Accordingly, in one option, the RFID-enabled AIMD external telemetry programmer system 138 will have a limited RFID interrogation transmit time and a time-out period.

The RFID-enabled external telemetry programmer of the present invention is capable of sending out a transmit pulse and receiving return signals from the RFID tags previously described within the patient. In the case where there is no return pulse, in the present invention the display will automatically read, "no tag detected" or something similar. In an MRI suite or emergency room situation, it is expected that as one gets a "no tag detected" reading, one would move the reader very close to the patient's implanted device and attempt to reinterrogate. If one again sees a "no tag detected" display, then one would have to assume that they have an old (legacy) device that does not have an embedded or implanted RFID tag. Under these circumstances, one would have to return to the old time-consuming routine of searching around the hospital for an interrogator programmer compatible with the implanted medical device.

FIG. 18 illustrates an RFID AIMD external programmer 146 in accordance with the present invention. Shown, is an RFID reader and interrogator antenna 164 attached by cable 148 to the AIMD external programmer 146. In this case, the external programmer 146 is an RF distance telemetry type with an RF antenna 166. The cable 148 is either hard-wired or plugged in to a pre-existing port 168 of the external telemetry programmer 146. This could be a USB port, a local area network (LAN) port also known as an RJ45 port, a fast Ethernet port, a CAT5, a CAT5e port, a CAT6 port, a firewire port (also known as IEEE1394i.LINK). A typical port on an AIMD external programmer 146 could also be a firewire 400 port. As illustrated, the RFID tag 124 is located in the wrist or forearm of the patient 160.

Figure 19:
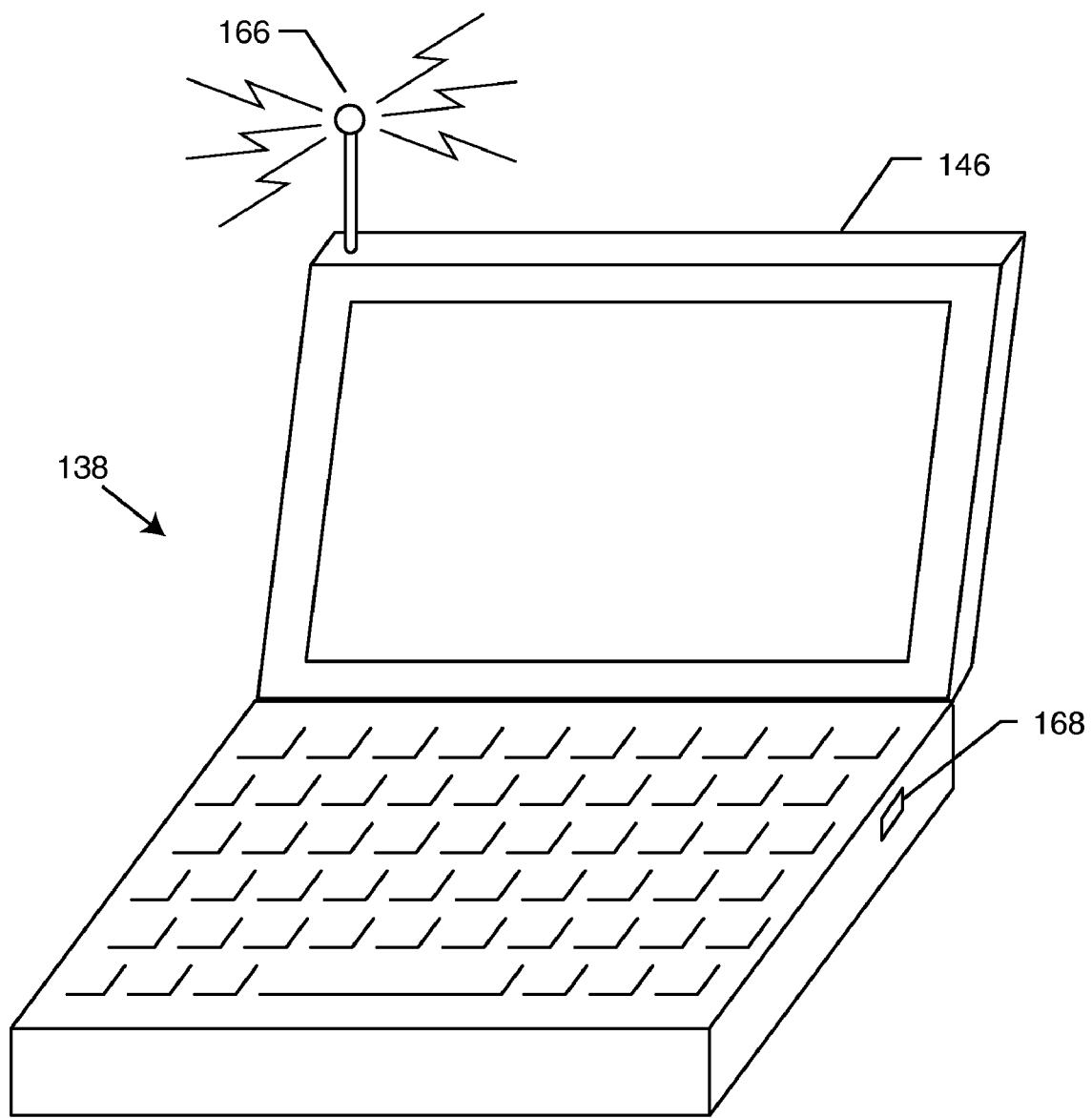
FIG. 19 illustrates an RFID-enabled AIMD external telemetry programmer in the form of a notebook computer.

FIG. 19 illustrates an RFID-enabled AIMD external telemetry programmer 146. In this case, the RFID reader/interrogator is entirely built into the AIMD external telemetry programmer 146 as a stand-alone unit. In other words, it has its own RFID signal generators and receiving circuitry and has its own built-in antenna 166 for creating and detecting RFID pulses. It also has its own internal software, including look-up tables. As a practical matter, look-up tables are an important feature of the present invention. That is, a typical RFID tag may only have 256 bits of information (unless it was a larger type). In other words, saving storage space in the RFID tag chip is important. For example, a designation code could be assigned to each different AIMD manufacturer. For example, Medtronic could be MDT, St. Jude Medical could be STS, and the like. Accordingly, only the transmission of three letters is required rather than transmitting the full text. In the case of FIG. 19, only the RFID antenna 166 is external to the AIMD external telemetry programmer 146, and all of these look-up table software features would be prewired or pre-programmed into the external AIMD programmer 146. In a preferred embodiment, the programmer keyboard and soft keys would be interactive with the RFID reader/interrogator antenna 166.

Accordingly, in view of all of the foregoing, it will be appreciated that the present invention relates to design modifications to prior art or newly designed AIMD external telemetry programmers to incorporate an enabled RFID interrogation system either attached to or built within them. In addition, it is important that such RFID interrogation systems have provisions such as limited transmit time and time-out period for protecting electronic devices, including medical devices, against RFID-associated electromagnetic interference (EMI).

More particularly, the present invention relates to an RFID-enabled AIMD external telemetry programmer system for identifying the MRI compatibility of implanted leads including those with inductors, energy dissipating surfaces or bandstop filters. An active implantable medical device (AIMD) includes electronic circuitry for therapy delivery or detection of biological signals, an electrode, and an implantable lead for connecting the electrode to the electronic circuitry. An inductance and/or a bandstop filter is placed in series with the lead and has electrical inductance in parallel with capacitance. The bandstop filter is resonant at a center frequency and attenuates current flow over a range of selective frequencies. An RFID tag is associated with the AIMD or the lead or the electrode, for identifying the presence of the bandstop filter in the AIMD or the lead or the electrode. An RFID-enabled external AIMD universal programmer transmits an electromagnetic signal to establish a communication link with the AIMD electronic chip.

The present invention may optionally include a circuit for limiting the total continuous transmit time of an electromagnetic signal, and a time-out circuit for delaying a subsequent transmission of the electromagnetic signal. By limiting the total continuous transmit time of the electromagnetic signals, in the case of a cardiac pacemaker, only a few heartbeats would be dropped, which is clinically insignificant to the patient. In a preferred embodiment, the total continuous transmit time of the electromagnetic signal is 500 milliseconds or less, and the time-out circuit delays the subsequent transmission of the electromagnetic signal for 2 seconds or more.

Although several embodiments have been described in detail for purposes of illustration, various modifications may be made without departing from the scope and spirit of the invention. Accordingly, the invention is not to be limited, except as by the appended claims.

What is claimed is:

1. An RFID-enabled AIMD programmer system for identifying the MRI compatibility of an implantable lead, the system comprising:

a) an implantable lead comprising a lead wire having a length extending from a proximal end that is electrically connectable to an active implantable medical device (AIMD) to a distal end electrically connected to an electrode, wherein a bandstop filter is electrically connected in series with the lead wire somewhere along the length thereof;
   b) an RFID tag attached to the implantable lead, the RFID tag having retrievable information relating to the MRI compatibility of the implantable lead under a static magnetic field or the ability of the bandstop filter to attenuate current flow through the lead at one or more selected frequencies or ranges of frequencies; and
   c) an RFID-enabled AIMD external telemetry programmer which is configured to transmit an electromagnetic signal to establish a communication link with the RFID tag.

2. The system of claim 1, wherein the implantable lead is selected from the group consisting of a lead that is electrically connectable to an active implantable medical device (AIMD), an abandoned lead, a lead connected to an abandoned lead cap, and a lead that is electrically connectable to an active external medical device.

3. The system of claim 1, wherein the implantable lead is electrically connected to an active implantable medical device (AIMD) having electronic circuitry for therapy delivery or detection of biological signals.

4. The system of claim 3, wherein in addition to having retrievable information relating to the MRI compatibility of the implantable lead, the RFID tag includes retrievable information relating to at least one of the group consistina of the active implantable medical device, a patient, and a physician.

5. The system of claim 4, including means for changing information stored in the RFID tag to correspond to changes in characteristics of at least one of the AIMD, the implanted lead, and a patient.

6. The system of claim 3, wherein the retrievable information further pertains to the magnetic resonance imaging (MRI) compatibility of the AIMD.

7. The system of claim 3, wherein the AIMD is selected from the group consisting of a cardiac pacemaker, an implantable defibrillator, a congestive heart failure device, a hearing implant, a neurostimulator, a ventricular assist device, a spinal cord stimulator, an implantable sensing system, a deep brain stimulator, an incontinence device, a vagus nerve stimulator, a bone growth stimulator, a gastric pacemaker, a Bion, a lead wire, and an abandoned lead.

8. The system of claim 1 or 3, wherein the electromagnetic signal of the AIMD external telemetry programmer is transmitted in an LF or an HF frequency range.

9. The system of claim 1, wherein the electromagnetic signal comprises an RFID communication signal.

10. The system of claim 1 or 9, wherein the AIMD external telemetry programmer comprises a read-only or a reader/writer device.

11. The system of claim 9, wherein the AIMD external telemetry programmer is configured for communication with a computer or a computer network.

12. The system of claim 11, including an electronic database or look-up table enabling the communication between the AIMD external telemetry programmer and the RFID tag.

13. The system of claim 12, wherein the electronic database or look-up table resides in the computer or computer network.

14. The system of claim 12, wherein the electronic database or look-up table resides in the AIMD external telemetry programmer.

15. The system of claim 1, wherein the electromagnetic signal is selected from the group consisting of an RFID interrogation signal, an RFID tag search signal, an RFID test signal, an RFID read signal, and an RFID write signal.

16. The system of claim 1, wherein the electromagnetic signal comprises a modulated signal.

17. The system of claim 1, wherein, when powered up, the AIMD external telemetry programmer is configured to actively search for or communicate with the RFID tag.

18. The system of claim 1, wherein the RFID tag comprises a read-only or a readable/writable RFID tag.

19. The system of claim 1, wherein the RFID tag comprises an antenna and an electronic micro-chip electrically connected to the antenna.

20. The system of claim 1, wherein the AIMD external telemetry programmer includes a circuit for limiting the total continuous transmit time of the electromagnetic signal, and a time-out circuit for delaying a subsequent transmission of the electromagnetic signal.

21. The system of claim 20, wherein the total continuous transmit time of the electromagnetic signal is no greater than five seconds.

22. The system of claim 20, wherein the time-out circuit delays the subsequent transmission of the electromagnetic signal for two seconds or more.

23. The system of claim 20, wherein the total continuous transmit time of the electromagnetic signal is 500 milliseconds or less.

24. The system of claim 20, including a switch in the RFID-enabled AIMD external telemetry programmer for temporarily actuating the total continuous transmit time limiting circuit and the time-out circuit.

25. The system of claim 1, wherein the electromagnetic signal comprises a modulated signal.

26. The system of claim 1 wherein the RFID tag includes information related to the MRI compatibility of the implantable lead under the static magnetic field of a strength ranging from 0.5 to 3.0 Tesla.

27. The system of claim 26 wherein the RFID tag is attached to the active implantable medical device.

28. The system of claim 26 wherein the RFID tag is attached to the lead.

29. The system of claim 26 wherein the RFID tag is carried on or in a patient.

30. The system of claim 26, wherein the retrievable information from the RFID tag includes a center frequency of attenuation for the bandstop filter.

31. The system of claim 26, wherein the RFID tag is attached to an object in close proximity to a patient being medically assisted by the active implantable medical device.

32. An RFID-enabled AIMD programmer system for identifying the MRI compatibility of an implanted lead, the system comprising:
a) an active implantable medical device (AIMD) having electronic circuitry for therapy delivery or detection of biological signals;
b) an implantable lead comprising a lead wire having a length extending from a proximal end that is electrically connected to the active implantable medical device (AIMD) to a distal end electrically connected to an electrode, wherein a bandstop filter is electrically connected in series with the lead wire somewhere along the length thereof;
c) an RFID tag attached to at least one of the implantable lead, the AIMD, and a patient, the RFID tag having retrievable information relating to the MRI compatibility of the implantable lead under a static magnetic field or the ability of the bandstop filter to attenuate current flow through the lead at one or more selected frequencies or ranges of frequencies; and
d) an RFID-enabled AIMD external telemetry programmer which is configured to transmit an electromagnetic signal to establish a communication link with the RFID tag.

33. The system of claim 32 wherein the RFID tag includes information related to the MRI compatibility of the implantable lead under the static magnetic field of a strength ranging from 0.5 to 3.0 Tesla.

34. An RFID-enabled AIMD programmer system for identifying the MRI compatibility of an implantable lead, the system comprising:
a) an implantable lead comprising a lead wire having a length extending from a proximal end that is electrically connectable to an active implantable medical device (AIMD) to a distal end electrically connected to an electrode, wherein a bandstop filter is electrically connected in series with the lead wire somewhere along the length thereof;
b) an RFID tag attached to the implantable lead, the RFID tag having retrievable information relating to the implantable lead; and
c) an RFID-enabled AIMD external telemetry programmer which is configured to transmit an electromagnetic signal to establish a communication link with the RFID tag, wherein the programmer includes a time-out circuit so that regardless whether an RFID tag is detected, or not, the programmer transmits a first electromagnetic signal having a first limited total continuous transmit time that is not greater than a defined transmit length, followed by an interim period of defined, manually non-resettable interim length where the time-out circuit renders the programmer incapable of transmitting the electromagnetic signal, followed by the programmer transmitting a second electromagnetic signal having a second limited total continuous transmit time that is not greater than the defined transmit length, and wherein no matter how frequently the programmer is actuated, the time-out circuit prevents the second and subsequent transmissions of the electromagnetic signal after a prior electromagnetic signal has been transmitted from the programmer until the interim period of the defined, manually non-resettable interim length has expired, and wherein the first, second and subsequent transmissions of the electromagnetic signal can be less, but not greater than, the defined transmit length.

35. The system of claim 34 wherein the total continuous transmit time of the electromagnetic signal is no greater than five seconds.

36. The system of claim 34 wherein the time-out circuit delays the subsequent transmission of the electromagnetic signal for two seconds or more.

37. The system of claim 34 wherein the total continuous transmit time of the electromagnetic signal is 500 milliseconds or less.

38. The system of claim 34 wherein the electromagnetic signal comprises a modulated signal.

39. The system of claim 34 including a switch in the RFID-enabled AIMD external telemetry programmer for temporarily actuating the total continuous transmit time limiting circuit and the time-out circuit.

* * * * *

UNITED STATES PATENT AND TRADEMARK OFFICE
CERTIFICATE OF CORRECTION

PATENT NO. : 8,321,032 B2
APPLICATION NO. : 12/871201
DATED : November 27, 2012
INVENTOR(S) : Frysz et al.

It is certified that error appears in the above-identified patent and that said Letters Patent is hereby corrected as shown below:

In the Claims:

Column 18, line 31, in claim 4, insert the word --consisting-- and delete the word "consistina"

Signed and Sealed this
Twenty-first Day of May, 2013

Teresa Stanek Rea
*Acting Director of the United States Patent and Trademark Office*